United States Patent [19]

Przyklek-Elling et al.

[11] Patent Number: 4,661,438
[45] Date of Patent: Apr. 28, 1987

[54] QUATERNIZED TELLURIUM SALT FOG INHIBITING AGENTS FOR SILVER HALIDE PHOTOGRAPHY

[75] Inventors: Rosemary Przyklek-Elling, Rochester; Wolfgang H. H. Gunther, Webster; Roger Lok, Hilton, all of N.Y.

[73] Assignee: Eastman Kodak Company, Rochester, N.Y.

[21] Appl. No.: 824,751

[22] Filed: Jan. 31, 1986

Related U.S. Application Data

[63] Continuation-in-part of Ser. No. 719,841, Apr. 4, 1985, abandoned.

[51] Int. Cl.[4] .................................................. G03C 1/34
[52] U.S. Cl. ...................................... 430/423; 430/446; 430/448; 430/570; 430/599; 430/614; 544/1
[58] Field of Search .............. 430/614, 570, 599, 423, 430/446, 448; 544/1

[56] References Cited

U.S. PATENT DOCUMENTS 4,576,905  3/1986  Gunther et al. ................... 430/401
4,581,330  4/1986  Gunther et al. ................... 430/611

OTHER PUBLICATIONS

*Research Disclosure*, vol. 176, Dec. 1978, Item 17643.
T. H. James, *The Theory of the Photographic Process*, 4th Edition, Macmillan, 1977, pp. 393–399.
Gunther et al., U.S. Ser. No. 660,155, filed Oct. 12, 1984, titled Photographically Useful Chalcogenazoles, Chalcogenazolines, and Chalcogenazolinium and Chalcogenazolium Salts.
Mbuyi et al., The 1,3-Benzotellurazole: A New Heterocyclic System, Tetrahedron Letters, vol. 24, No. 52, pp. 5873–5876, 1983.

*Primary Examiner*—Won H. Louie
*Attorney, Agent, or Firm*—Carl O. Thomas

[57] ABSTRACT

Radiation sensitive silver halide photographic elements are disclosed which are protected from fog by quaternized aromatic oxatellurazinium salts. The aromatic oxatellurazinium salts can be initially incorporated in the photographic element as manufactured or during processing.

26 Claims, No Drawings

QUATERNIZED TELLURIUM SALT FOG INHIBITING AGENTS FOR SILVER HALIDE PHOTOGRAPHY

This is a continuation-in-part of U.S. Ser. No. 719,841, filed Apr. 4, 1985, now abandoned.

FIELD OF THE INVENTION

This invention relates to photography. It relates to silver halide photographic elements, to imaging processes, and to novel compounds useful therewith.

BACKGROUND OF THE INVENTION

In the course of processing a photographic element containing an imagewise exposed silver halide emulsion layer reduced silver can be formed either as a direct or inverse function of exposure. At the same time, at least a low level of reduced silver formation also occurs independently of imagewise exposure. The term "fog" is herein employed to indicate the density of the processed photographic element attributable to the latter, usually measured in minimum density areas. In color photography fog is typically observed as image dye density rather than directly as silver density.

Over the years a variety of materials have been introduced into silver halide emulsions to inhibit the formation of fog. *Research Disclosure*, Vol. 176, December 1978, Item 17634, Section VI, lists the more commonly employed fog inhibiting agents *Research Disclosure* is published by Kenneth Mason Publications Limited; Emsworth; Hampshire P010 7DD; England. From Section VI it is apparent that useful fog inhibiting agents are highly diverse in their structural forms, ranging from halide ions (e.g. bromide salts) to inorganic metal salts to specific polymers to selected acyclic organic compounds to specific heterocycles. These useful fog inhibiting agents have been selected from among a plethora of structurally similar, but relatively ineffective compounds. Useful fog inhibiting agents have been largely identified empirically. T. H. James, *The Theory of the Photographic Process*, 4th Ed., Macmillan, 1977, pp. 393–399, in grouping and suggesting various performance mechanisms for fog inhibiting agents illustrates their diversity.

Gunther et al U.S. Ser. No. 660,155, filed Oct. 12, 1984, titled PHOTOGRAPHICALLY USEFUL CHALCOGENAZOLES, CHALCOGENAZOLINES, AND CHALCOGENAZOLINIUM AND CHALCOGENAZOLIUM SALTS, commonly assigned, now U.S. Pat. No. 4,576,905, discloses to be useful as intermediates in synthesizing aromatic tellurazolium salts compounds containing a 1,2,5-oxatellurazinium ring fused with an aromatic ring. The synthesis taught by Gunther et al results in the nitrogen atom of the 1,2,5-oxatellurazinium ring being protonated. Specifically, oxatellurazinium salts satisfying formula (I)

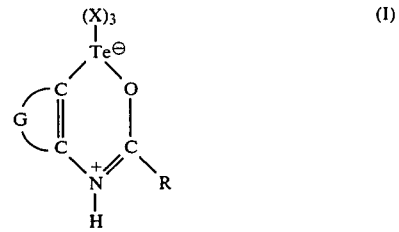

are prepared by reacting a compound according to formula (II)

with tellurium tetrachloride or tellurium tetrabromide at an elevated temperature, wherein:

H* is an activated hydrogen atom,

G represents the atoms completing an aromatic nucleus,

R represents an aliphatic or aromatic group comprised of a hydrocarbon moiety optionally linked through a divalent oxy, thio, or carbonyl linkage, an amino group, an amido group, a ureido group, a formamidine disulfide group, or a —C(O)M group, wherein M is chosen to complete an acid, ester, thioester, or salt, and X represents chloride or bromide or another halogen or a pseudohalogen substituted therefor after preparation.

Repeated attempts to prepare a quaternized oxatellurazinium salt by substituting a quaternizing substituent for the hydrogen atom bonded to the nitrogen atom in formula (II) have uniformly met with failure. Thus, Gunther et al teaches protonated oxatellurazinium salts and does not disclose or suggest a feasible method of preparing quaternized oxatellurazinium salts.

Lok et al U.S. Ser. No. 702,545, filed Feb. 19, 1985, now U.S. Pat. No. 4,581,330, titled TELLURIUM SALT FOG INHIBITING AGENTS FOR SILVER HALIDE PHOTOGRAPHY, commonly assigned, discloses the oxatellurazinium salts of Gunther et al to be useful fog inhibiting agents. Lok et al discloses only the method of Gunther et al for preparing the oxatellurazinium salts.

SUMMARY OF THE INVENTION

In one aspect this invention is directed to quaternized oxatellurazinium salts as novel compounds.

In another aspect this invention is directed to a photographic element containing a radiation sensitive silver halide emulsion and an effective amount of a fog inhibiting agent characterized in that the fog inhibiting agent is a quaternized aromatic oxatellurazinium salt.

In another aspect this invention is directed to a process of producing a photographic image comprising processing a photographic element containing at least one imagewise exposed silver halide emulsion in the presence of an effective amount of a fog inhibiting agent characterized in that the fog inhibiting agent is a quaternized aromatic oxatellurazinium salt.

The present invention permits the use of photographic elements containing radiation sensitive silver halide emulsions to produce photographic images exhibiting low levels of fog. The invention affords an alternative approach to fog reduction and in many instances fog reduction compares favorably with fog reduction achieved by other commonly employed and highly effective fog inhibiting agents.

DESCRIPTION OF PREFERRED EMBODIMENTS

The present invention has been made possible by the discovery of a process for preparing quaternized oxatellurazinium salts. Specifically it has been discovered that quaternized oxatellurazinium salts satisfying formula (III)

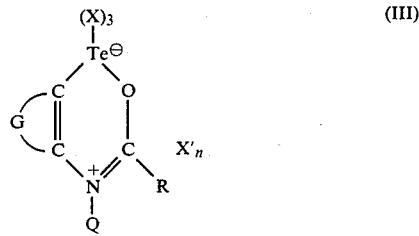

are prepared by reacting a quaternized aromatic tellurazolium salt according to formula (IV)

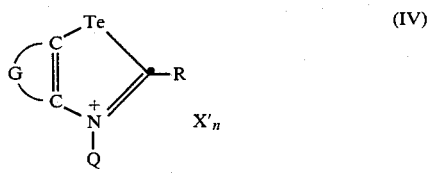

with chlorine or bromine in the presence of oxygen, wherein

G represents the atoms completing an aromatic nucleus;
R represents hydrogen, an aliphatic or aromatic group comprised of a hydrocarbon moiety optionally linked through a divalent oxy, thio, or carbonyl linkage, an amino group, an amido group, a ureido group, a formamidine disulfide group, or a —C(O)M group, wherein M is chosen to complete an aldehyde, acid, ester, thioester or salt;
Q represents a quaternizing substituent;
X represents chloride or bromide as initially prepared, but which can be extended to another halogen or a pseudohalogen by subsequent substitution;
X' represents a charge balancing counter ion; and
n represents the integer 0 or 1.

The reaction can be conveniently performed by dissolving the quaternized tellurazolium salt of formula (IV) in solution. Water is a useful solvent. Other solvents can be chosen from a wide range of relatively unreactive organic solvents, such as acetonitrile, dimethylsulfoxide, dimethylformamide, dichloromethane, methanol, ethanol, or isopropyl alcohol Elemental bromine or chlorine can be dissolved in the aqueous solution containing the quaternized tellurazolium salt. For example, liquid bromine can be added directly to the aqueous solution. Chlorine can be dissolved in the aqueous solution by bubbling chlorine gas. Alternatively, elemental bromine or chlorine can be generated in the aqueous solution by adding bromine or chlorine releasing compounds and a strong nonoxidizing acid, such as hydrochloric acid, hydrobromic acid, sulfuric acid, fluoroboric acid, a sulfonic acid, or phosphoric acid. For example, elemental bromine can be readily released into the aqueous solution by introducing an alkali bromate, N-bromosuccinimide, or alkali hydrobromite. Elemental chlorine can be conveniently released by introducing an alkali hypochlorite.

Generally the reaction of the quaternized aromatic tellurazolium salt and the elemental bromine or chlorine present in the aqueous solution occurs spontaneously at room temperature. In most instances the reaction appears to occur substantially instantaneously. The ring oxygen atom in the aromatic oxatellurazinium salt can be spontaneously supplied from ambient air.

Although the compound of formula (III) as initially prepared restricts the choice of X to chloride or bromide, if desired, the chloride or bromide in the formula (III) compound can be displaced by iodide or a pseudohalogen by treatment with an iodide or pseudohalogen salt. The term "pseudohalogen" is employed to designate any one of the recognized class of substituents known to approximate the substituent properties of halogen, such as a cyano, thiocyanate, or hydroxy substituent. Thus, X in formula (III) can be halogen (employed here and elsewhere to designate generically chloride, bromide, or iodide) or pseudohalogen. In a specifically preferred form X is chloride or bromide.

In general the aromatic nuclei, which form G in each of its various occurrences and are referred to in other occurrences variously as aromatic rings, nuclei, or aryl groups or moieties, are preferably carbocyclic aromatic nuclei having from 6 to 20 carbon atoms, most preferably a phenyl or naphthyl or, in the fused form, a benzo or naphtho nucleus. In some instances an aromatic nucleus can be fused through a five-membered ring, as illustrated by acenaphthylene fused at its 1,2 ring edge.

The aromatic nucleus represented by G can be either substituted or unsubstituted. Turning back to formula (II), in part the reaction to produce the material of formula (I) is accomplished by choosing G in formula (II) so that the aromatic nucleus which it completes is activated in the position ortho to the amido substituent. This can be accomplished by including in the aromatic nucleus one or more substituents capable of directing ring substitution in formula (II) to the ring position of the starred activated hydrogen atom. For carbocyclic aromatic rings, such as benzene and naphthene rings, useful substituents can be chosen from among aliphatic and aromatic groups comprised of hydrocarbon moieties (e.g., alkyl, aryl, alkaryl, or alkaryl) optionally linked through a divalent oxygen or sulfur atom (e.g., an alkoxy, aryloxy, alkaryloxy, alkaryloxy, alkylthio, arylthio, alkarylthio, or alkarylthio group); an amino group, including primary, secondary and tertiary amines; an amido group (e.g., acetamido and butyramido); a sulfonamido group (e.g. an alkyl or arylsulfonamido group); a sulfamoyl group (e.g. an alkyl or arylsulfamoyl group); a ureido group (e.g., 1-ureido, 3-phenyl-1-ureido, and 3-methyl-1-ureido); a thioureido group (e.g., a thioureido group corresponding to the above exemplary ureido groups); hydroxy; or a —C(O)M group or —S(O)$_2$M group, wherein M is chosen to complete an acid, ester, thioester, or salt (e.g., —C(O)OH, —C(O)SCH$_3$, —C(O)OCH$_3$, —C(O)ONa, —S(O)$_2$OH, —S(O)$_2$OCH$_2$C$_6$H$_5$, or —S(O)$_2$OLi). While the same substituents of the aromatic nucleus G in formula (II) can be present in each occurrence of G, specifically the occurrence of formula (III), it is appreciated that, since the compounds of formula (II) are not employed to prepare the compounds of formula (III), G in formula (III) includes both unsubstituted aromatic nuclei and those having a broader range of values.

The substituent R can take any synthetically convenient form. R can include hydrogen, an aliphatic or aromatic group comprised of a hydrocarbon moiety (e.g., alkyl, aryl, alkaryl, or aralkyl moiety) optionally linked through a divalent oxy, thio, or carbonyl linkage (e.g., an alkoxy, aryloxy, alkaryloxy, aralkyloxy, alkylthio, arylthio, alkarylthio, aralkylthio, or acyl moiety); an amino group, including primary, secondary and tertiary amines; an amido group (e.g., acetamido and butyramido); a ureido group (e.g., 1-ureido, 3-phenyl-1-ureido, and 3-methyl-1-ureido); a formamidine disulfide group (e.g., formamidine disulfide and N'-ethyl-N'-methyl-α,α'-dithiobisformamidine groups); or a —C(O)M group, wherein M is chosen to complete an aldehyde, acid, ester, thioester, or salt (e.g., —C(O)H, —C(O)OH, —C(O)OCH$_3$, —C(O)SCH$_3$, or —C(O)ONa). When R is a primary amino group, it is in fact in one tautomeric form an imino group, which provides a convenient reaction site for further substitution.

The quaternizing substituent Q in formulae (III) in general corresponds to the quaternizing substituent present in the quaternized aromatic tellurazolium salt of formula (IV). However, since preparation of the quaternized oxatellurazinium salt requires bromine or chlorine treatment, it is apparent that any quaternizing substituent of the aromatic tellurazolium salt that is susceptible to bromine or chlorine addition will be modified. For example, quaternizing groups containing vinyl or acetylenic unsaturation will be bromine or chlorine substituted if present in the quaternized aromatic tellurazolium salt.

The choice of quaternizing substituents can be better appreciated by noting that the aromatic tellurazolium salt of formula (IV) can be prepared by reacting a tellurazole satisfying formula (V)

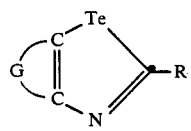

with a quaternizing agent. In one preferred form the quaternizing agent is a sulfonic acid ester containing the quaternizing radical Q as the alcohol derived moiety of the ester. Specifically preferred quaternizing agents are strong quaternizing agents, such as poly(fluoro)alkylsulfonic acid esters, such as alkyl, aryl, alkenyl, alkynyl, aralkyl, or alkaryl esters of poly(fluoro)alkylsulfonic acid. Perfluorinated alkylsulfonic acid esters are particularly preferred quaternizing agents (e.g., trifluoromethylsulfonic acid esters). Arylsulfonic acid esters, such as para-toluenesulfonic acid esters, are also strong quaternizing agents. 1,3,2-Dioxathiane-2,2-dioxide and 1,3,2-di-oxathiolane-2,2-dioxide have also been demonstrated to be useful quaternizing agents. Including electron donating ring substituents in the aromatic nuclei forming G in formula (V) facilitates quaternization while strongly electron withdrawing substituents require strong quaternizing agents to be employed when quaternization occurs after tellurazole ring formation.

In one specifically preferred form the quaternizing substituent Q can take the form disclosed in Freeman et al U.S. Ser. No. 712,495, filed Mar. 18, 1985, titled HYDROLYZED AZOLIUM SPEED ENHANCING-/FOG-INHIBITING AGENTS FOR SILVER HALIDE PHOTOGRAPHY, commonly assigned, now U.S. Pat. No. 4,578,348. In this form Q represents a quaternizing substituent having a divalent group satisfying formula (VI):

where:
T is carbonyl (CO) or sulfonyl (SO$_2$);
T$^1$ is independently carbonyl (CO) or sulfonyl (SO$_2$) in each occurrence; and
m is an integer of from 1 to 3.

In a specific preferred form the quaternizing substituent, e.g. Q, can take the form represented by formula (VII):

wherein
T, T$^1$, and m are as defined above;
L represents a divalent linking group, such as an optionally substituted divalent hydrocarbon group; and
R$^5$ represents an optionally substituted hydrocarbon residue or an amino group.

In preferred embodiments of the invention T is carbonyl and T$^1$ is sulfonyl. However, either or both of T and T$^1$ can be either carbonyl or sulfonyl. Further, where m is greater than 1, T$^1$ can in each occurrence be carbonyl or sulfonyl independently of other occurrences.

L is preferably an alkylene (i.e., alkanediyl) group of from 1 to 8 carbon atoms. In specifically preferred forms of the invention L is either methylene (—CH$_2$—) or ethylene (—CH$_2$CH$_2$—).

R$^5$ is preferably a primary or secondary amine, an alkyl group of from 1 to 8 carbon atoms (e.g., methyl, ethyl, propyl, i-propyl, n-butyl, i-butyl, t-butyl, neopentyl, or n-octyl), or an aryl group of from 6 to 10 carbon atoms (e.g., phenyl or naphthyl). When R$^5$ completes a secondary amine, it can be substituted with an optionally substituted hydrocarbon residue, preferably an alkyl group of from 1 to 8 carbon atoms or an aryl group of 6 to 10 carbon atoms, as above described.

m is in a preferred form the integer 1.

The counter ion X' in formulae (III) and (IV) can be any convenient ion which imparts charge neutrality to the compound. When no ionic substituents are present in the quaternized aromatic tellurazolium salt of formula (IV), the counter ion X' is an anion and n is 1. When the quaternized aromatic tellurazolium salt is a betaine, n is zero, since no counter ion is required. In formula (III), in the absence of ionized substituents, the aromatic oxatellurazinium salt is a betaine and no external charge balancing counter ion is required. When the quaternizing substituent includes an anionic group, such as a sulfo group, X' is a cation and n is 1.

Gunther et al, cited above, discloses oxatellurazinium salts to be useful intermediates for the preparation of various protonated aromatic tellurazolium salts. By treatment with a base a protonated aromatic tellurazolium salt can be converted to an aromatic tellurazole satisfying formula (V). This compound can thereafter be quaternized in the manner noted above to produce the quaternized aromatic tellurazolium salt of formula (IV).

By employing a quaternized aromatic oxatellurazinium salt the corresponding aromatic tellurazolium salt can be produced directly, thereby allowing elimination of the intermediate steps of preparing a protonated aromatic tellurazolium salt and then converting it to the corresponding aromatic tellurazole prior to quaternization. Thus, substitution of a quaternized aromatic oxatellurazinium salt according to formula (III) for a corresponding protonated aromatic oxatellurazinium salt of formula (I) permits a simplified procedure for the preparation of quaternized oxatellurazolium salts.

The quaternized aromatic oxatellurazinium salts of this invention also have utility as fog inhibiting agents. The quaternized oxatellurazinium salts of this invention when employed as fog inhibiting agents are preferably incorporated in the photographic element to be protected prior to exposure and processing—e.g., at the time of manufacture. When the quaternized oxatellurazinium salt is being relied upon to reduce fog the origin of which antedates processing, it is essential that the quaternized oxatellurazinium salt be incorporated in the silver halide emulsion layer or layers to be protected. It is generally most convenient to introduce the quaternized oxatellurazinium salt into the silver halide emulsion after precipitation of the emulsion and before coating.

When the quaternized oxatellurazinium salt is intended to become active at the time of processing, it can be incorporated within the photographic element at any location which permits permeation of one or more silver halide emulsion layers being imagewise developed. For example, the quaternized oxatellurazinium salt can be located in one or more silver halide emulsion layers or other hydrophilic colloid layers, such as in an overcoat, interlayer, or subbing layer. When the quaternized oxatellurazinium salt is intended to become active at the time of processing, it is generally most convenient to add the quaternized oxatellurazinium salt as a component of a processing solution, such as predevelopment bath or a developer, allowing it to permeate the silver halide emulsion layer or layers prior to or during development.

Any amount of quaternized oxatellurazinium salt effective to reduce fog can be employed. Optimum amounts of fog inhibiting agents for specific applications are usually determined empirically by varying concentrations. Such investigations are typically relied upon to identify optimum fog reduction concentrations or an optimum balance between fog reduction and other effects, such as reduction in photographic speed. When the quaternized oxatellurazinium salt is incorporated in a silver halide emulsion prior to coating, concentrations of from about 5.0 to 0.005 millimole per silver mole, preferably 0.5 to 0.01 millimole per silver mole, and optimally from 0.15 to 0.015 millimole per silver mole are contemplated. When the quaternized oxatellurazinium salt is incorporated in a processing solution, concentration ranges from minimum effective amounts—e.g., typically at least 0.05 millimole per liter—to up to about 0.5 millimole per liter are contemplated.

It is, of course, recognized that conventional fog inhibiting agents, such as those illustrated by *Research Disclosure*, Item 17643, Section VI, cited above, can be employed in combination with oxatellurazinium salts in the practice of this invention. Since it is recognized that fog inhibiting agents operate by a variety of differing mechanisms, as illustrated by James, cited above, the effects produced by combinations of quaternized oxatellurazinium salts and conventional fog inhibiting agents will range from highly interdependent to independently additive, but in any case optimum concentrations are susceptible to empirical determination. It is specifically contemplated that quaternized oxatellurazinium salts can be employed in combination with protonated oxatellurazinium salts of the type shown in formula (I) above.

In addition to the fog inhibiting agent this invention in one form additionally requires a photographic element containing a radiation sensitive silver halide emulsion. These silver halide emulsions can be comprised of silver bromide, silver chloride, silver iodide, silver chlorobromide, silver chloroiodide, silver bromoiodide, silver chlorobromoiodide or mixtures thereof. The emulsions can include silver halide grains of any conventional shape or size. Specifically, the emulsions can include coarse, medium or fine silver halide grains of either regular (e.g., cubic or octahedral) or irregular (e.g., multiply twinned or tabular) crystallographic form. Recently developed high aspect ratio tabular grain emulsions, such as those disclosed by Wilgus et al U.S. Pat. No. 4,434,266, Daubendiek et al U.S. Pat. No. 4,414,310, Wey U.S. Pat. No. 4,399,215, Solberg et al U.S. Pat. No. 4,433,048, Mignot U.S. Pat. No. 4,386,156, Jones et al U.S. Pat. No. 4,478,929, Maskasky U.S. Pat. No. 4,400,463, Wey et al U.S. Pat. No. 4,414,306, and Maskasky U.S. Pat. No. 4,435,501, are specifically contemplated. Sensitizing compounds, such as compounds of copper, thallium, lead, bismuth, cadmium and Group VIII noble metals, can be present during precipitation of the silver halide emulsion, as illustrated by Arnold et al U.S. Pat. No. 1,195,432, Hochstetter U.S. Pat. No. 1,951,933, Trivelli et al U.S. Pat. No. 2,448,060, Overman U.S. Pat. No. 2,628,167, Mueller et al U.S. Pat. No. 2,950,972, Sidebotham U.S. Pat. No. 3,488,709 and Rosecrants et al U.S. Pat. No. 3,737,313.

The silver halide emulsions can be either monodispersed or polydispersed as precipitated. The grain size distribution of the emulsions can be controlled by silver halide grain separation techniques or by blending silver halide emulsions of differing grain sizes. The emulsions can include Lippmann emulsions and ammoniacal emulsions, as illustrated by Glafkides, *Photographic Chemistry*, Vol.1, Fountain Press, London, 1958, pp.365–368 and pp.301–304; excess halide ion ripened emulsions as described by G. F. Duffin, *Photographic Emulsion Chemistry*, Focal Press Ltd., London, 1966, pp.60–72; thiocyanate ripened emulsions, as illustrated by Illingsworth U.S. Pat. No. 3,320,069; thioether ripened emulsions, as illustrated by McBride U.S. Pat. No. 3,271,157, Jones U.S. Pat. No. 3,574,628 and Rosecrants et al U.S. Pat. No. 3,737,313 or emulsions containing weak silver halide solvents, such as ammonium salts, as illustrated by Perignon U.S. Pat. No. 3,784,381 and *Research Disclosure*, Vol.134, June 1975, Item 13452.

The emulsions can be surface-sensitive emulsions—i.e., emulsions that form latent images primarily on the surfaces of the silver halide grains—or internal latent image-forming emulsions—i.e., emulsions that form latent images predominantly in the interior of the silver halide grains, as illustrated by Knott et al U.S. Pat. No. 2,456,953, Davey et al U.S. Pat. No. 2,592,250, Porter et al U.S. Pat. Nos. 3,206,313 and 3,317,322, Bacon et al U.S. Pat. No. 3,447,927, Evans U.S. Pat. No. 3,761,276, Morgan U.S. Pat. No. 3,917,485, Gilman et al U.S. Pat. No. 3,979,213 and Miller U.S. Pat. No. 3,767,413.

The emulsions can be negative working emulsions, such as surface-sensitive emulsions or unfogged internal latent image-forming emulsions, or direct-positive emulsions of the unfogged, internal latent image-forming type, which are positive working when development is conducted with uniform light exposure or in the presence of a nucleating agent, as illustrated by Ives U.S. Pat. No. 2,563,785, Evans U.S. Pat. No. 3,761,276, Knott et al U.S. Pat. No. 2,456,953 and Jouy U.S. Pat. No. 3,511,662.

Blends of surface sensitive emulsions and internally fogged, internal latent image-forming emulsions can be employed, as illustrated by Luckey et al U.S. Pat. Nos. 2,996,382, 3,397,987 and 3,705,858, Luckey U.S. Pat. No. 3,695,881, *Research Disclosure*, Vol.134, June 1975, Item 13452, Millikan et al Defensive Publication T-904017, Apr. 21, 1972 and Kurz *Research Disclosure*, Vol. 122, June 1974, Item 12233.

The quaternized oxatellurazinium salts are preferably employed to reduce fog in negative working silver halide emulsions and most preferably those that contain silver halide grains which form surface latent images on exposure.

The silver halide emulsions can be surface sensitized. Noble metal (e.g., gold), middle chalcogen (e.g., sulfur, selenium, or tellurium), and reduction sensitizers, employed individually or in combination are specifically contemplated. Typical chemical sensitizers are listed in *Research Disclosure*, Item 17643, cited above, Section III.

The silver halide emulsions can be spectrally sensitized with dyes from a variety of classes, including the polymethine dye class, which includes the cyanines, merocyanines, complex cyanines and merocyanines (i.e., tri-, tetra-, and poly-nuclear cyanines and merocyanines), oxonols, hemioxonols, styryls, merostyryls, and streptocyanines. Illustrative spectral sensitizing dyes are disclosed in *Research Disclosure*, Item 17643, cited above, Section IV.

The silver halide emulsions as well as other layers of the photographic elements of this invention can contain as vehicles hydrophilic colloids, employed alone or in combination with other polymeric materials (e.g., latices). Suitable hydrophilic materials include both naturally occurring substances such as proteins, protein derivatives, cellulose derivatives—e.g., cellulose esters, gelatin—e.g., alkali treated gelatin (cattle, bone, or hide gelatin) or acid treated gelatin (pigskin gelatin), gelatin derivatives—e.g., acetylated gelatin, phthalated gelatin, and the like, polysaccharides such as dextran, gum arabic, zein, casein, pectin, collagen derivatives, collodion, agar-agar, arrowroot, and albumin. The vehicles can be hardened by conventional procedures. Further details of the vehicles and hardeners are provided in *Research Disclosure*, Item 17643, cited above, Sections IX and X.

The silver halide photographic elements of this invention can contain other addenda conventional in the photographic art. Useful addenda are described, for example, in *Research Disclosure*, Item 17643, cited above. Other conventional useful addenda include desensitizers, couplers (such as dye forming couplers, masking couplers and DIR couplers) DIR compounds, anti-strain agents, image dye stabilizers, absorbing materials such as filter dyes and UV absorbers, light scattering materials, antistatic agents, coating aids, plasticizers and lubricants, and the like.

The photographic elements of the present invention can be simple black-and-white or monochrome elements comprising a support bearing a layer of the silver halide emulsion, or they can be multilayer and/or multicolor elements. The photographic elements produce images ranging from low contrast to very high contrast, such as those employed for producing half tone images in graphic arts. They can be designed for processing with separate solutions or for in-camera processing. In the latter instance the photographic elements can include conventional image transfer features, such as those illustrated by *Research Disclosure*, Item 17643, cited above, Section XXIII. Multicolor elements contain dye image forming units sensitive to each of the three primary regions of the spectrum. Each unit can be comprised of a single emulsion layer or of multiple emulsion layers sensitive to a given region of the spectrum. The layers of the element, including the layers of the image forming units, can be arranged in various orders as known in the art. In an alternative format, the emulsion or emulsions can be disposed as one or more segmented layers, e.g., as by the use of microvessels or microcells, as described in Whitmore U.S. Pat. No. 4,387,154.

A preferred color photographic element according to this invention comprises a support bearing at least one blue sensitive silver halide emulsion layer having associated therewith a yellow dye forming coupler, at least one green sensitive silver halide emulsion layer having associated therewith a magenta dye forming coupler and at least one red sensitive silver halide emulsion layer having associated therewith a cyan dye forming coupler, at least one of the silver halide emulsion layers containing an oxatellurazinium salt fog inhibiting compound.

The elements of the present invention can contain additional layers conventional in photographic elements, such as overcoat layers, spacer layers, filter layers, antihalation layers, scavenger layers and the like. The support can be any suitable support used with photographic elements. Typical supports include polymeric films, paper (including polymer-coated paper), glass and the like. Details regarding supports and other layers of the photographic elements of this invention are contained in *Research Disclosure*, Item 17643, cited above, Section XVII.

The photographic elements can be imagewise exposed with various forms of energy, which encompass the ultraviolet, visible, and infrared regions of the electromagnetic spectrum as well as electron beam and beta radiation, gamma ray, X ray, alpha particle, neutron radiation, and other forms of corpuscular and wave-like radiant energy in either noncoherent (random phase) forms or coherent (in phase) forms, as produced by lasers. When the photographic elements are intended to be exposed by X rays, they can include features found in conventional radiographic element, such as those illustrated by *Research Disclosure*, Vol. 184, August 1979, Item 18431.

Processing of the imagewise exposed photographic elements in the presence of the quaternized oxatellurazinium salt need not differ from conventional processing. Processing procedures, developing agents, and development modifiers are illustrated by *Research Disclosure*, Item 17643, cited above, Sections XIX, XX, and XXI, respectively. In its preferred application the invention relates to silver halide photographic elements which are processed in aqueous alkaline developers in the presence of the quaternized aromatic oxatellurazinium salt.

While the quaternized oxatellurazinium salts have been disclosed to be useful as fog inhibiting agents in silver halide photographic elements, it is appreciated that they can have more general utility as oxidizing agents. The fog inhibiting activity of the quaternized oxatellurazinium salts is attributable to their ability to oxidize silver metal atoms that would otherwise catalyze silver halide development to silver ions. It is therefore apparent that the quaternized oxatellurazinium salts are capable of similarly oxidizing metals lying higher in the electromotive series of elements than silver.

The quaternized aromatic tellurazolium salts employed as starting materials for the preparation of the quaternized aromatic oxatellurazinium salts of this invention can be prepared as taught by Gunther et al, cited above. As noted above, Gunther et al first prepares a corresponding protonated aromatic tellurazolium salt which is converted to the corresponding aromatic tellurazole by treatment with a base and then quaternized. The protonated aromatic tellurazolium salt can be presented by formula (VIII):

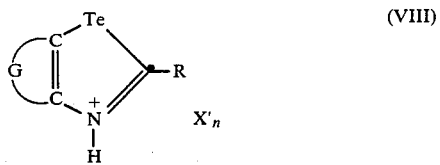

wherein G, R, n, and X' are as previously defined.

A first process for preparing a protonated tellurazolium salt satisfying the general formula (VIII) comprises
  reacting a starting material of the formula

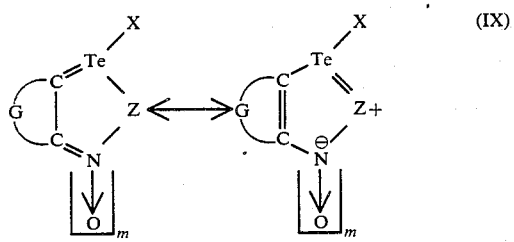

with a strong alkaline reducing agent,
  acylating with a compound of the formula

and
  treating with a strong nonoxidizing acid,
wherein
  G represents the atoms completing a fused aromtic nucleus,
  R is an optionally substituted hydrocarbon moiety,
  m is zero or 1,
  X is halogen or pseudohalogen,
  Y is halogen or R—C(O)—O—,
  Z is —O— or —N(R')—, and R' is an aromatic nucleus.

A second process for preparing a protonated tellurazolium salt satisfying general formula (VIII) comprises reacting a starting material of the formula

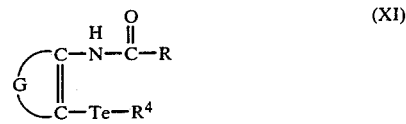

with phosphoryl chloride or bromide wherein:
  G represents the atoms completing an aromatic nucleus,
  R represents hydrogen, an optionally substituted hydrocarbon moiety, or a —C(O)M group, wherein M is chosen to complete an aldehyde, acid, ester, thioester, or salt, and
  $R^4$ represents a leaving group.

A third process for preparing a protonated tellurazolium salt satisfying general formula (VIII) comprises
  reacting a starting material of formula (I) with a strong alkaline reducing agent, and
  treating with a strong monoxidizing acid.

The starting material according to formula (I) is prepared by reacting a compound according to formula (II) tellurium tetrachloride or tetrabromide at an elevated temperature.

The first process for preparing a protonated tellurazolium salt satisfying formula (VIII) described above employs a starting material satisfying formula (IX). When m is zero and Z is —N(R')—, the starting material can be (2-phenylazophenyl-C,N')tellurium(II) chloride, the preparation of which is described by Cobbledick et al, "Some New Organotellurium Compounds Derived from Azobenzene: The Crystal and Molecular Structure of (2-Phenylazophenyl-C,N')tellurium(II) Chloride", $Journal$ $of$ $Chemical$ $Research$, pp. 1901-1924, 1979. Although Cobbledick et al employed chloride as the halogen corresponding to X in formula (IX), it is apparent from the reported synthesis that X can be any halogen or a pseudohalogen substituent. Similarly, G and R' can be varied merely by substituting for one or both of the phenyl groups employed in the phenylazophenyl employed by Cobbledick et al an alternative aromatic nucleus.

In an alternative form the first process can employ a starting material according to formula (IX) in which m is zero and Z is oxygen. This compound can be formed by placing in solution an optionally substituted α-tetralone, hydrochloric or hydrobromic acid, tellurium dioxide, and hydroxylamine. This reaction has the advantage that all of the required materials are readily available at relatively low cost. Alcohols are convenient solvents for the reaction, although other nonreactive organic solvents can be employed. Heating is not required, but can accelerate the reaction. The material of formula (IX) forms a solid phase which can be separated by routine filtering and washing steps. Both unsubstituted α-tetralone and various substituted derivatives are useful. Preferred α-tetralones can be represented by the formula (XII):

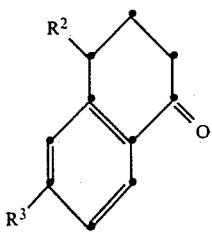

(XII)

wherein R[2] and R[3] are independently selected from among hydrogen, halogen, alkyl, and alkoxy. Since R[2] and R[3] are naphtho ring substituents in the tellurazolium salt ultimately produced, it is apparent that the number of carbon atoms in the alkyl and alkoxy substituents can be widely varied. Instead of employing an α-tetralone, as described above, it is possible to employ a substituted or unsubstituted acenaphthen-1-one.

In general alkyl substituents and moieties of the tellurazolium salts and their derivatives are limited only by physical considerations, such as solubility, mobility, and molecular bulk. Generally alkyl and other aliphatic moieties of the tellurazolium salts and their derivatives of this invention are contemplated to contain up to 18 or more carbon atoms. Since increasing molecular bulk, except as sometimes required to reduce mobility, is seldom desirable in photographic applications, the preferred aliphatic hydrocarbon moieties contain up to 6 carbon atoms, with the lower alkyls (i.e., methyl, ethyl, propyl, and butyl) being preferred. In general, references to cycloalkyl indicate groups having 4 to 10 carbon atoms in a ring, with 5 or 6 ring carbon atoms being preferred.

Instead of preparing the starting material of formula (IX) wherein m is zero and Z is oxygen in the manner described above, an oxime of an α-tetralone or acenaphthen-1-one described above can be reacted with tellurium tetrahalide, preferably tellurium tetrachloride or tellurium tetrabromide. In this and subsequent descriptions of employing tellurium tetrahalides as reactants it should be borne in mind that similar results can usually be obtained by reacting, before or during the α-tetralone or acenaphthen-1-one reaction, a soluble halide salt, such as an alkali or alkaline earth halide, with tellurium dioxide. This is believed to generate a tellurium tetrahalide. A carboxylic acid can be employed as a solvent for the reaction, and the reaction can be accelerated by heating. The starting material of formula (IX) forms a solid phase which can be separated by routine filtering and washing procedures. The preferred α-tetralone oximes correspond to the preferred α-tetralones and can be represented by formula (XIII):

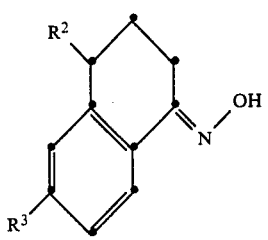

(XIII)

wherein R[2] and R[3] are chosen as described above.

In a third general form of the starting material of formula (IX) m can be 1 and Z oxygen. This form of the starting material of formula (IX) can be prepared by reacting with tellurium tetrahalide a carbocyclic aromatic compound activated for electrophilic substitution. Although naphthalene is illustrative of a fused ring carbocyclic aromatic compound that has been activated for electrophilic substitution, it is generally easiest to activate benzene. Activation can be achieved by employing electron donating substituents, such as hydroxy, hydroxyalkyl, alkyl, alkoxy, aryloxy, hydroxyaryl, amino, and groups of similar negative Hammett sigma values, singly or in combination. The reaction can be carried out in an organic solvent such as a liquid hydrocarbon (e.g., benzene or cyclohexane), a halohydrocarbon (e.g., chlorobenzene or chloroform), a nitrohydrocarbon (e.g., nitromethane), or acetonitrile while heating to reflux. Formation of the starting material of formula (IX) can be completed by nitrating and then treating with a reducing agent. Strong reducing agents can be employed in precisely stoichiometric concentrations or less. It is generally preferred to employ a mild or dilute reducing agent. Nitric acid in a suitable diluent, such as water or carboxylic acid, can be used for nitrating while hypophosphorous acid can be employed as the mild reducing agent. The synthetic route described above can be modified by a preliminary treatment with the mild reducing agent before nitrating and employing a strong nonoxidizing acid after nitrating and before employing the mild reducing agent a second time. In general the strong nonoxidizing acids contemplated for use in this and other steps of the preparation procedures herein described include acids such as hydrochloric acid, hydrobromic acid, sulfuric acid, fluoroboric acid, a sulfonic acid, and phosphoric acid.

A particularly preferred starting material prepared by the process described in the preceding paragraph can be represented by formula (XIV):

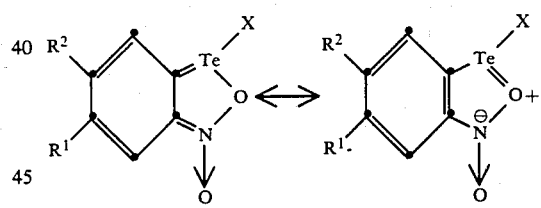

(XIV)

wherein at least one of R[1] and R[2] and preferably both are chosen from among hydroxy, hydroxyalkyl, alkyl, alkoxy, aryloxy, hyroxyaryl, and amino groups. Alternately R[1] and R[2] together can form an alkanediyldioxy linkage—e.g., a —O—(CH$_2$)$_n$—O— linkage, where n is preferably from 1 to 3. X is halogen or pseudohalogen, as previously described.

Once the starting material of formula (IX) has been prepared, regardless of the choice of alternative preparation routes described above, it is treated with a strong alkaline reducing agent, such as an alkali borohydride (e.g., lithium, sodium, or potassium borohydride). The reaction product is then acylated with a compound according to formula (X). From the values of Y identified above, it is apparent that the acylating agent can be either acyl halide, such as acetyl chloride or acetyl bromide, or an acid anhydride, such as acetic anhydride. By noting the appearance of R in formulae (VIII) and (X) it is also apparent that the acyl halide or acid anhydride also provides the 2-position substituent in the protonated tellurazolium salt formed as an ultimate product. Generally this R is a methyl group, but a wide variety of alternatives can be generated readily, if desired. When the acylating agent is acetyl halide or acetic anhydride, the 2-position substituent is methyl. By varying the acyl halide or acid anhydride employed, the 2-position substituent of the tellurazolium salt can take the form of various hydrocarbon moieties, such as alkyl, cycloalkyl, alkaryl, aryl, aralkyl, and various substituted derivatives, such as those containing alkoxy, alkylthio, halo, amino, amido, and similar substituents.

Though not isolated, it is believed that acylation produces tellurazolines. To avoid opening of the tellurium containing ring, the additional step of producing the stable corresponding protonated tellurazolium salt is undertaken by treatment with a strong nonoxidizing acid, such as any of those mentioned above.

The second process for preparing protonated tellurazolium salts according to formula (VIII) allows a somewhat more general selection of R or 2-position ring substituents as compared to the first process. The starting material employed for this process is represented by formula (XI). When the second process is employed, R in the starting material of formula (XI) and the protonated tellurazolium salt prepared satisfying formula (VIII) can include in addition to any of the optionally substituted hydrocarbon moieties discussed above in connection with the first process hydrogen or a —C(O)M group, wherein M is chosen to complete an aldehyde, acid, ester, thioester, or salt (e.g., —C(O)H, —C(O)OH, —C(O)OCH$_3$, —C(O)SCH$_3$, or —C(O)ONa). When M completes an ester or thioester, the esterifying moiety can take any of the hydrocarbon or substituted hydrocarbon form(s) previously described by reference to R.

R$^4$ in formula (XI) forms no part of the protonated tellurazolium salt ultimately produced. Thus, R$^4$ can take the form of any convenient group that can be displaced upon treatment with phosphoryl chloride to permit ring closure. Treatment with phosphoryl chloride eliminates Cl—R$^4$. Thus, any group that can be eliminated as the chloride can be chosen as the leaving group. For example, R$^4$ can be chosen from among the same hydrocarbon moieties described above in connection with R. Since R$^4$ forms no part of the protonated tellurazolium salt ultimately produced, it is generally most convenient to select R$^4$ from among lower alkyl substituents.

The starting material of formula (XI) can be prepared from known tellurium compounds by several alternative procedures. One preferred approach is to start with a compound according to formula (IX) in which m is zero and Z is —N(R')—, as previously described. This compound is treated with a strong alkaline reducing agent, such as previously described. Thereafter, acylation is performed using an acylating agent according to formula (X), as previously described. This produces the material of formula (XI). To produce the starting material of formula (XI) by another procedure, after treating the above compound of formula (IX) with a strong alkaline reducing agent, the reaction product is reacted with X—R$^4$, where X is halide, and then acylated with formic acid. In this instance R in formula (XI) is hydrogen. By employing other acylating agents R can take any one of the other forms of formula (XI).

A third process for preparing a protonated tellurazolium salt according to formula (VIII) comprises employing a starting material according to formula (I). X in formula (I) can be halogen or pseudohalogen, as previously described. R in the starting material of formula (I) can taken an even greater variety of forms than described above in connection with formula (XI). R in the starting material of formula (I) and the protonated tellurazolium salt prepared satisfying formula (VIII) can include an aliphatic or aromatic group comprised of a hydrocarbon moiety (e.g., alkyl, aryl, alkaryl, or aralkyl moiety) optionally linked through a divalent oxy, thio, or carbonyl linkage (e.g., an alkoxy, aryloxy, alkaryloxy, aralkyloxy, alkylthio, arylthio, alkarylthio, aralkylthio, or acyl moiety); an amino group, including primary, secondary and tertiary amines; an amido group (e.g., acetamido and butryamido); a ureido group (e.g., 1-ureido, 3-phenyl-1-ureido, and 3-methyl-1-ureido); a formamidine disulfide group (e.g., formamidine disulfide and N'-ethyl-N'-methyl-α,α'-dithiobisformamidine groups); or a —C(O)M group, wherein M is chosen to complete an aldehyde, acid, ester, thioester, or salt (e.g., —C(O)H, —C(O)OH, —C(O)OCH$_3$, —C(O)SCH$_3$, or —C(O)ONa). The starting material is reacted with a strong alkaline reducing agent, such as described above, and the resulting product is reacted with a strong nonoxidizing acid, such as also described above, to produce the desired protonated tellurazolium salt. By suitable treatment, (e.g., reduction or hydrolysis), the formamidine disulfide can, if desired, be converted to a thioureido group once the protonated tellurazolium salt has been formed. (The structure of formamidine disulfide is described in *International Union of Pure and Applied Chemistry, Nomenclature of Organic Chemistry*, Butterworths, London, 1965, Section 951.5.) When R is a primary amino group, it is in fact in one tautomeric form an imino group, which provides a highly convenient starting material for the synthesis of azacyanine dyes.

When any commonly available compound of formula (II) is melted or heated in a suitable solvent (e.g., acetonitrile, butyronitrile, or chloroform) with tellurium tetrachloride or tellurium tetrabromide, the material of formula (I) is produced. Heating to a temperature of at least 60° C. up to about 140° C. is contemplated, with temperatures of from about 110° to 120° C. being preferred. As noted above, G in formula (II) is chosen so that the aromatic nucleus which it completes is activated in the position ortho to the amido substituent. The aromatic nucleus completed by G as well as R can progress unaltered from the compound of formula (II) to the protonated tellurazolium salt of formula (VIII).

To obtain the tellurazole corresponding to the protonated tellurazolium salt prepared as described above treatment with a base, such as ammonium hydroxide, an alkali hydroxide, or an alkali carbonate or bicarbonate, can be undertaken. Procedures for performing the same operation on known chalcogenazolium salts are directly applicable.

Gunther et al, in addition to teaching the formation of a quaternized aromatic tellurazolium salt by first preparing a protonated aromatic tellurazolium salt, converting it to the corresponding tellurazole, and then quaternizing, teaches an alternative preparation approach. This approach for preparing quaternized tellurazolium salts according to formula (IV) is to employ a starting material according to formula (IX) wherein m is zero, indicated specifically by formula (XV):

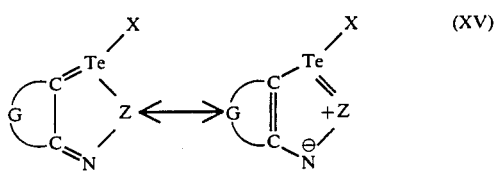

wherein G, X, and Z are as indicated in formula (IX). The starting material is first treated with a strong alkaline reducing agent, which can be selected from among those described above. The reaction product is then treated with an oxidizing agent, such as oxygen, a peroxide, or a sulfoxide, to produce the compound of formula (XVI)

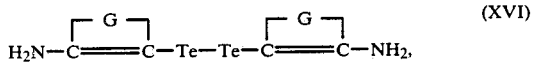

which is treated with an aldehyde, treated with a strong alkaline reducing agent, such as described above, and then treated with an acylating agent according to formula (X), as described above, and a strong nonoxidizing acid, also as described above. Although treatment with an oxidizing agent is preferred, no separate oxidizing step is required. Ambient air will spontaneously perform such oxidation, and treatment with the aldehyde is sufficient in an inert atmosphere. Employing this approach, a variety of quaternizing substituents can be introduced in the salt of formula (IV) in addition to those provided by strong quaternizing agents, merely by appropriate selection of the aldehyde. Thus, Q in formula (IV) can take the form of an optionally substituted hydrocarbon residue of an aldehyde quaternizing substituent, such as alkyl, alkenyl, alkynyl, or aralkyl moieties as well as substituted derivatives, such as oxy, thio, sulfo, sulfonyl, sulfato, halo, or carboxy substituted derivatives, often incorporated to modify solubility or other physical properties. Sulfoalkyl and sulfatoalkyl quaternizing substituents having from 1 to 6 carbon atoms are specifically preferred.

EXAMPLES

The following examples further illustrate the quaternized oxatellurazinium salts of the invention and their preparation from previously published starting materials. Preparations of compounds of types that have been previously published are labeled by letters (e.g., A, B, C, etc.). Preparations of starting materials not previously published are included among the examples.

A.

Preparation of 2-Phenylazophenyltellurium Trichloride

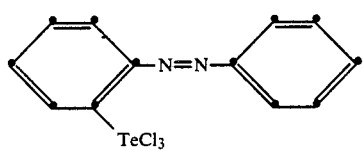

$C_{12}H_9Cl_3N_2Te$  mw=415.18

A two liter, 3-necked flask was fitted with mechanical stirrer (Teflon ® blade), reflux condenser and nitrogen inlet. A gas outlet from the top of the condenser was connected to a gas bubbler dipping into a magnetically stirred 1000 ml beaker containing 200 ml distilled water and a little phenolphthalein indicator. The system was sufficiently gas tight so that a very gentle steam of nitrogen produced consistent bubbles in the indicator solution.

Into the flask were placed 100 g (0.55 mole) azobenzene, 134 g (0.5 mole) tellurium tetrachloride, and 66 g (0.5 mole) anhydrous aluminum chloride. 1,2-Dichlorobenzene (500 ml) was added, the apparatus closed, the nitrogen flow started, and the mixture stirred until an orange-brown solution was obtained. Five ml of 1N sodium hydroxide were then added to the indicator solution, and the flask contents were heated to reflux with brisk stirring. The start of the reaction was marked by loss of the indicator color. Measured volume increments of 1N sodium hydroxide were then added to the beaker each time the indicator color discharged. Incremental volume and elapsed time of addition are tabulated below:

| Time Minutes | Vol. in NaOH ml |
|---|---|
| 0 | 5 |
| 6.5 | 50 |
| 13.0 | 100 |
| 20.0 | 150 |
| 28.0 | 200 |
| 36.5 | 250 |
| 46.0 | 300 |
| 54.0 | 350 |
| 70.0 | 400 |
| 85.0 | 450 |
| 94.0 | 475 |

Boiling under reflux was continued until 475 ml 1N sodium hydroxide had been consumed. The flask contents were then permitted to cool to about 80° C. Methyl alcohol was then added very slowly to the rapidly stirred solution until the initial vigorous reaction ceased. A total of 500 ml methanol was then added and the mixture cooled in ice for more than one hour. The heavy granular crystalline precipitate was collected by filtration and washed with methanol until the methanol filtrate was pale yellow.

The light brown glittering crystals were dried in vacuum. A yield of 130.3 g (63% of theory), m.p. 261°–263° C. was obtained. The product contained small amounts of oxides that were removed by recrystallization from 1,2-dichlorobenzene. Elemental analyses of the recrystallized product were in agreement with the structural formula.

B.

Preparation of 3,4-Dimethoxyphenyltellurium Trichloride $C_8H_9Cl_3O_2Te$  mw=371.13

1,2-Dimethoxybenzene (veratrole, 13.8 g=0.1 mole) and tellurium tetrachloride (26.9 g=0.1 mole) were heated in chloroform (120 ml) for 2 hours under reflux and with stirring. After 30 minutes yellow crystals started to precipitate. The product (25.2 g, 67.9% of theory) was collected by filtration and dried in a vacuum oven, m.p. 162°–163° C. (dec. with gas evolution). The mass spectra were in agreement with that of the structural formula.

C.

Preparation of Bis(3,4-dimethoxyphenyl)ditelluride $C_{16}H_{18}O_4Te_2$  mw=529.42

3,4-Dimethoxyphenyltellurium trichloride (37.2 g=0.1 mole) was dissolved in absolute ethanol (500 ml), and the slightly turbid solution was filtered. To the rapidly stirred solution was added, at room temperature, 50% aqueous hypophosphorous acid (30 ml, ≈0.3 mole) as rapidly as possible. There was a brief appearance of a brown solution color, before the entire solution set to a mass of black fibrous crystals. The product was collected after 15 minutes by filtration using rubber dam to compact the highly solvated crystal mass. The product was washed with water and then air dried to yield 25.2 g, 95% of theory, black fibrous crystals, m.p. 134°–136° C. Recrystallization from isopropanol raised the m.p. to 136°–139° C. C, H and Te elemental analyses were in agreement with the structural formula.

λ-max=305 nm ε-max=1.006×10⁴

EXAMPLE 1

1-Chloro-5,6-dimethoxy-2,1,3-benzoxatellurazole-N-oxide

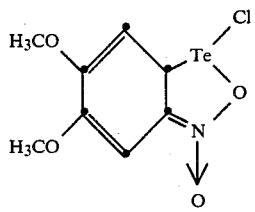

$C_8H_8ClNO_4Te$ 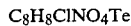 mw=345.21

A.

By nitration of product of Preparation C

Bis(3,4-dimethoxyphenyl)ditelluride (10 g=0.018 mole) was added in small portions to 70 mole percent nitric acid (15 ml) with stirring and chilling in ice. The material dissolved rapidly with emission of nitrous fumes. The mixture was then warmed at ≈40° C. for 30 minutes and subsequently stirred at room temperature for one hour. Emission of orange fumes was no longer observed. Water (150 ml) was then added to the orange solution resulting in a yellow precipitate, which (5 g) was mixed with ethanol (100 ml) and concentrated hydrochloric acid (20 ml), then diluted with water to 200 ml (just prior to occurrence of precipitation). Hypophosphorous acid (5 ml of 50 mole percent) was then added. During 15 minutes of stirring at room temperature, a deep red precipitate appeared which was collected by filtration. The product was recrystallized from absolute ethanol (450 ml) to give red prisms, (2.5 g), m.p. 197°–200° C. The yield by this procedure calculated to be ≈32%.

B.

By nitration and reduction of product of Preparation B 3,4-Dimethoxyphenyltellurium trichloride (74 g=0.2 mole) was suspended in glacial acetic acid (200 ml) in a 1500 ml Erlenmeyer flask. Nitric acid (18 g of 70%=0.2 mole) was added gradually to the stirred mixture, which caused formation of a clear, red solution and a mildly exothermic reaction. Stirring was continued for one hour at room temperature, then ethanol (1000 ml) and hypophosphorous acid (24.0 g of 50 weight percent aqueous) were added in order. Over a period of 30 minutes there occurred crystallization of a red solid, which was collected by filtration to give 47.3 g, 68.8% of theory, m.p. 199°–200° C. The material was identical to product isolated by procedure A. Elemental analyses were in agreement with that calculated for the structural formula.

EXAMPLES 2–5

Examples 2 through 5 illustrate the preparation of compounds according to the following general formula

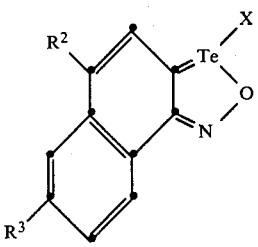

EXAMPLE 2

3-Chloronaphth[2,1-c]-1,2,5-oxatellurazole $R^3=R^2=H, X=Cl$ $C_{10}H_6ClNOTe$  mw=319.22

Tellurium dioxide (80 g, 0.5 mole) was dissolved in concentrated hydrochloric acid (200 ml, 2.0 moles) with stirring. When solution was complete, a suspension of hydroxylamine hydrochloride (69 g, 1.0 mole) in ethyl alcohol (300 ml) was added. When all solid was dissolved, α-tetralone (73 g, 0.5 mole) in ethyl alcohol (1200 ml) was added. The clear reaction mixture rapidly turned red and dark crystals began to form within an hour. After the reaction mixture had been kept five days at room temperature, the product was isolated by room temperature, the product was isolated by filtration and dried in a vacuum. Yield 123.2 g.

The product was separated from elemental tellurium by continuous extraction with dichloromethane in a Soxhlet extractor, using about 1300 ml of solvent. Chilling the extract yielded a first crop of 84.9 g. Diluting the filtrate with twice its volume of heptane yielded a second crop of 6.1 g. The combined yield of 91.0 g represented a 57% yield. mp. 182°–183° C. λ-max (in pyridine) was 503 nm. ε-max=0.82×10⁴. C, H, Cl, N, O and Te elemental analyses results and the mass spectra were in agreement with those expected for the structural formula.

EXAMPLE 3

3-Bromonaphth[2,1-c]-1,2,5-oxatellurazole $R^3=R^2=H, X=Br$ $C_{10}H_6BrNOTe$  mw=363.68

Alpha-tetralone oxime (24 g=0.05 mole), tellurium dioxide (35 g=0.22 mole), lithium bromide (60 g), and acetic acid (350 ml) were combined, and the mixture was heated to a gentle boil for 20 minutes. The precipitated solid was collected by filtering the reaction mixture hot and washing the product with water to give 38.9 g, 71% of theory, of a deep maroon solid. The product was recrystallized from carbon tetrachloride (m.p. 183°–185° C.) Elemental analyses and the mass spectra were in agreement with the those expected for structural formula.

EXAMPLE 4

3-Chloro-5-methylnaphth[2,1-c]-1,2,5-oxatellurazole $R^3=H$, $R^2=CH_3$, $X=Cl$ $C_{11}H_8ClNOTe$   mw=333.24

Tellurium dioxide (79.5 g=0.5 mole) was dissolved in concentrated hydrochloric acid (200 ml). Hydroxylamine hydrochloride (35 g=0.5 mole) was added and then ethanol to bring the total volume to 2000 ml. To the slightly turbid solution was added 4-methyl-α-tetralone (80 g=0.5 mole) and the stirred mixture heated briefly to boil. The clear deep red solution was then kept overnight at room temperature. The solid mass of crystalline product was collected, washed well with water and dried in a vacuum oven at 90° C. to give a first crop (111.1 g) of dark red needles. The filtrate was heated once again and kept at room temperature for 24 hours. A second crop of 14.3 g crude product was obtained. The well-dried product was placed into a Soxhlet thimble and extracted with methylene chloride. The majority of purified product crystallized from the solvent during the course of the extraction to give a yield of 97.0 g=58.3% of theory, m.p. 196°–198° C. Elemental analyses results were in agreement with the structural formula. The ultraviolet and visible spectra in dichloromethane showed three maxima.

| | |
|---|---|
| λ-max 507 nm | ε-max = 1.21 × 10⁴ |
| λ-max 300 nm | ε-max = 1.06 × 10⁴ |
| λ-max 256 nm | ε-max = 2.30 × 10⁴ |

EXAMPLE 5

3-Chloro-7-methoxynaphth[2,1-c]-1,2,5-oxatellurazole $R^3=OCH_3$, $R^2=H$, $X=Cl$ $C_{11}H_8ClNO_2Te$   mw=349.24

This compound was prepared in the same general way as the corresponding compound of Example 4, except that 6-methoxy-α-tetralone (88.1 g=0.5 mole) was used as the starting ketone. The step of heating of the reaction mixture to boil and then keeping it at room temperature was repeated three times, giving a combined crude yield of 84.8 g. Recrystallization by Soxhlet extraction with dichloromethane gave 72.5 g, 41.5% yield, of small dark needles (m.p. 237°–239° C.). Elemental analyses results were in agreement with the structural formula. The ultraviolet and visible spectra in dichloromethane showed four maxima.

| | |
|---|---|
| 510 nm | ε-max = 0.89 × 10⁴ |
| 454 nm | ε-max = 0.93 × 10⁴ |
| 312 nm | ε-max = 0.81 × 10⁴ |
| 245 nm | ε-max = 2.63 × 10⁴ |

EXAMPLE 6

1-Chloroacenaphtho[1,2-d]-2,1,5-oxatellurazole

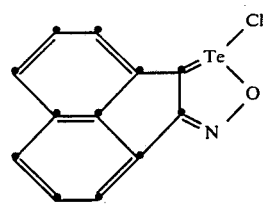

Acenaphthylen-1-one (83.5 g, 0.05 mole), hydroxylamine hydrochloride (35 g, 0.05 mole), and tellurium dioxide (80 g, 0.05 mole) were combined in ethanol (3 l). The mixture was heated to reflux and maintained at that temperature for an hour. It was then allowed to cool to room temperature and stirring at room temperature continued for 12 days. The solid was isolated by filtration, washed with ethanol, and air dried. Yield of brown powder was 106 g. This was extracted with toluene in a Soxlet extractor. The yield of product was 67.6 g, 46% of theory. The ultraviolet and visible spectra in dichloromethane solution showed four maxima, at 489.6, 429, 372, and 316 nanometers.

EXAMPLES 7–11

These examples refer to 1,1,1-trihalo (substituted) 2,1,4-benzoxatellurazinium, inner salts.

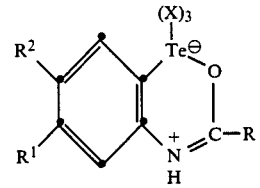

EXAMPLE 7

1,1,1-Trichloro-6-methoxy-3-methyl-2,1,4-benzoxatellurazinium, inner salt $R^1=OCH_3$, $R^2=H$, $R=CH_3$, $X=Cl$ $C_9H_{10}Cl_3NO_2Te$   mw=398.05

3-Methoxyacetanilide, (34 g=0.2 mole) and tellurium tetrachloride (54 g=0.2 mole) were jointly stirred into chloroform (100 ml) in a 500 ml Erlenmeyer flask. After an initial solution had been formed, the mass set solid with a fine yellow precipitate. The mixture was immersed in an oil bath kept at 115° C. The mixture was manually stirred until all solids had redissolved or melted. After most of the chloroform had evaporated, there resulted a clear yellow melt that rapidly became opaque while gaseous HCl was being emitted. The temperature was raised to 120° C. and heating continued with occasional manual stirring until the entire mass had set to a brittle solid. The reaction was terminated after 2 hours. Ethanol was added to the still hot reaction mixture to disperse the product. Recrystallization from ethanol (1300 ml) yielded colorless needles (47.1 g, 59% of theory), m.p. 245°–246° C.

C, H, N and Te elemental analyses were in agreement with those calculated for the structural formula.

EXAMPLE 8

1,1,1-Trichloro-3,6-dimethyl-2,1,4-benzoxatellurazinium, inner salt

R=R¹=CH₃, R²=H, X=Cl $C_9H_{10}Cl_3NOTe$   mw=392.05

3-Methylacetanilide (m-acetotoluidide) (82 g=0.55 mole) and tellurium tetrachloride (148 g, 0.55 mole) were combined with chloroform (300 ml) and the mixture heated for 20 hours in an oil bath kept at 115° C. with continuous removal of HCl. The hot reaction product was dispersed in ethanol (200 ml) and the product collected by filtration to give a yield of 149 g, 71% of theory, colorless prisms, m.p. >300° C. for analyses the compound was recrystallized from boiling acetonitrile.

The elemental analyses were in agreement with those expected for the structural formula.

EXAMPLE 9

1,1,1-Trichloro-3,6,7-trimethyl-2,1,4-benzoxatellurazinium, inner salt

R=R¹=R²=CH₃, X=Cl $C_{10}H_{12}Cl_3NOTe$   mw=396.07

3,4-Dimethylacetanilide (56 g=0.37 mole) was combined with TeCl₄ (100 g, 0.37 mole) in acetonitrile (100 ml) and immersed in an oil bath, first for one hour at 120° C. and then for 3 more hours at 130° C. Additional acetonitrile was added, and the partial solution was chilled. The product was collected by filtration to give 74.7 g, 52% of theory, colorless crystals, m.p. >300° C. after darkening at >280° C. Recrystallization from acetonitrile required 400 ml solvent for 15 g of the substance. C, H, Cl, N and Te elemental analyses were in agreement with those expected for the structural formula.

EXAMPLE 10

1,1,1-Trichloro-3-methyl-6-methylthio-2,1,4-benzoxatellurazinium, inner salt

R=CH₃, R¹=SCH₃, R²=H, X=Cl $C_9H_{10}Cl_3NOSTe$   mw=413.95

3-Methylthioacetanilide (68 g=0.37 mole), prepared by acetylation of commercial 3-methylthioaniline, was combined with TeCl₄ (100 g=0.37 mole) in chloroform (100 ml). The mixture was heated for 3 hours in an oil bath kept at 130° C., then introduced hot into acetonitrile (300 ml), chilled, and filtered. A crystalline solid yielding 68 g, 49% of theory was obtained. For analysis the material was recrystallized from boiling acetonitrile (100 ml dissolves ≃4 g) with the aid of decolorizing charcoal and was recovered as lustrous, pale yellow prisms, m.p. 251°-253° C. The elemental analyses were in agreement with those expected for the structural formula.

EXAMPLE 11

1,1,1-Trichloro-6-hydroxy-3-methyl-2,1,4-benzoxatellurazinium, inner salt

R=CH₃, R¹=OH, R²=H, X=Cl $C_8H_8Cl_3NO_2Te$   mw=383.95

3-Hydroxyacetanilide (60 g=0.4 mole) and TeCl₄ (107.6 g=0.4 mole) were combined in acetonitrile (80 ml) and the mixture immersed for 2 hours in an oil bath maintained at 120° C. To the hot melt was then added enough acetonitrile to make a paste. The mixture chilled overnight and filtered with suction to give 86.5 g, 56% of theory, colorless crystalline solid. For analysis this was recrystallized from hot acetonitrile, where 25 g required 150 ml of solvent and gave a recovery of 10 g colorless needles, m.p. 247°-248° C. The elemental analyses were in agreement with that expected for the structural formula.

D.

Preparation of Bis(2-acetamido-4-methoxyphenyl)ditelluride $C_{18}H_{20}N_2O_4Te_2$   mw=583.23

1,1,1-Trichloro-6-methoxy-3-methyl-2,1,4-benzoxatellurazinium, inner salt (Example 11) (5.0 g=0.0125 mole) was dissolved in 50% aqueous ethanol (200 ml). The solution heated to boil, and hydrazine (1 ml) was added with stirring. The deep orange solution was cooled slowly to room temperature to deposit fibrous needles which, upon filtration and drying, yielded a tan solid (3.25 g, 89% theory), m.p. 181°-182° C.

EXAMPLES 12-17

Examples 12 through 17 illustrate the preparation of benzotellurazolium hydro salts

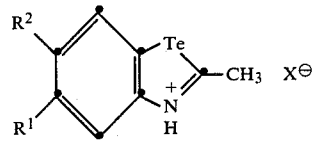

EXAMPLE 12

5,6-Dimethoxy-2-methylbenzo-3H-tellurazolium Chloride

R¹=R²=OCH₃, X=Cl $C_{10}H_{12}ClNO_2Te$   mw=341.26

1-Chloro-5,6-dimethoxy-2,1,3-benzoxatellurazole-N-oxide (Example 1) (103 g=0.3 mole) was suspended in a mixture of tetrahydrofuran (1000 ml) and methanol (150 ml) using a 3 liter, 3 necked flask fitted with a stirrer, a nitrogen inlet, a reflux condenser, and a powder addition funnel. Under nitrogen, sodium borohydride (61.5 g-1.6 mole) was added gradually to the stirred solution until the color was a pale cream. The amount of borohydride was determined empirically by the disappearance of the starting material red color. The reaction mixture was then chilled, and acetic anhydride was added until the color had turned a bright orange. This required 41.3 g=0.4 mole acetic anhydride. The reaction was permitted to proceed for 10 minutes, and then concentrated hydrochloric acid (300 ml) was added in one portion. The mixture turned black immediately, indicating that considerable quantities of tellurium had been generated.

The black mixture was stirred for another 30 minutes, then filtered to collect the precipitate. The solid was washed briefly with dichloromethane and air dried. The crude product was then added to 1200 ml boiling methanol containing a little hydrochloric acid and filtered hot with the aid of Celite ® diatomaceous earth. The filtrate was chilled overnight to give pale grey crystals (15.6 g). Two more crops of product were extracted from the black solid, giving a total yield of 21.34 g, 19.9% of theory. For further purification, the material was recrystallized from boiling water containing a little hydrochloric acid. The pale cream colored needles did not have a distinct melting point, but decomposed gradually >150° C.

EXAMPLE 13

5-Methoxy-2-methyl-3H-benzotellurazolium Chloride $R^1 = OCH_3$, $R^2 = H$, $X = Cl$ $C_9H_{10}ClNOTe$          mw = 311.24

1,1,1-Trichloro-6-methoxy-3-methyl-2,1,4-benzoxatellurazinium, inner salt (Example 7) (40 g=0.1 mole) was suspended in methanol (400 ml), and a solution of sodium hydroxide (8.0 g=0.2 mole) in water (75 ml) was added. This formed a clear solution which was placed into a vessel fitted with a stirrer, a nitrogen inlet, and a condenser. Under nitrogen, sodium borohydride (10.6 g, 0.28 mole) was added in small increments until the solution no longer turned red or orange with further additions, eventually turning colorless. Partway into the reduction, the mixture solidified, but liquified again as the reduction progressed. To the suspension, which had been cooled to ≃10° C., was then added concentrated hydrochloric acid (100 ml) in one portion. The precipitate was filtered after 15 minutes (yield 42 g dark solid), and the filtrate was chilled for a second crop of 12 g solids. The first crop was recrystallized from 700 ml of hot water containing a little hydrochloric acid. The recovery was 16.1 g of almost white needles. The second crop also contained sodium chloride. It was recrystallized from 125 ml methanol, also containing a little hydrochloric acid, to give 3.6 g product. The combined yield of 19.7 g represented 63% of theory. For analysis, the material was crystallized once more from acidic methanol, 105° C. (sinter), 130°–135° C. (turned black), no clear melt >270° C.

EXAMPLE 14

2,5-Dimethyl-3H-benzotellurazolium Chloride $R^1 = CH_3$, $R^2 = H$, $X = Cl$ $C_9H_{10}ClNTe$          mw = 295.24

1,1,1-Trichloro-3,6-dimethyl-2,1,4-benzoxatellurazinium, inner salt (Example 8) (17.3 g=0.05 mole) was dissolved in a mixture of methanol (300 ml) and 1N sodium hydroxide (100 ml, 0.1 mole) in a vessel fitted with a nitrogen inlet, a condenser, and a magnetic stirrer. Through the condenser was added sodium borohydride until further addition no longer produced a transient orange color. This required about 3.0 g. The mixture was stirred for a few minutes under nitrogen, then concentrated hydrochloric acid (100 ml) was added in one portion. The mixture was clarified by filtration with Celite ®, then evaporated under reduced pressure to 200 ml, again filtered from inorganic salts and chilled overnight. Filtration yielded yield 9.15 g of colorless solid, which was rinsed with isopropanol and air dried. The material was not pure and contained inorganic salt contaminants.

EXAMPLE 15

2,5,6-trimethyl-3H-benzotellurazolium Chloride $R^1 = R^2 = CH_3$, $X = Cl$ $C_{10}H_{12}ClNTe$          mw = 309.25

1,1,1-Trichloro-3,6-7-trimethyl-2,1,4-benzoxatellurazinium, inner salt (Example 9) (39.6 g=0.1 mole) was placed into 400 ml of methanol in a 1000 ml, three necked flask fitted with a stirrer, a nitrogen inlet, a condenser, and a powder addition funnel. Sodium hydroxide (8.0 g=0.2 mole) in water (30 ml) was added, followed by sodium borohydride (8.56 g=0.225 mole) until the reduction mixture was a pale brown. This required heating to aid in dissolving the starting material and the initial reduction products. When the reduction was complete, the mixture was cooled to about 10° C., and concentrated hydrochloric acid (100 ml) was added in one portion. There was a granular black precipitate, which was removed by filtration. The filtrate was evaporated in vacuum to ≃250 ml, diluted with water to twice the volume, and stirred until crystallization was complete. A yield of 29.5 g, 94.8% of theory, was obtained. After two recrystallizations from methanol, the salt melted at 180°–184° C. (dec.).

EXAMPLE 16

2-Methyl-5-methylthio-3H-benzotellurazolium Chloride $R^1 = SCH_3$, $R^2 = H$, $X = Cl$ $C_9H_{10}ClNSTe$          mw = 327.30

1,1,1-Trichloro-3-methyl-6-methylthio-2,1,4-benzoxatellurazinium, inner salt (Example 10) (20.7 g=0.05 mole) was placed in methanol (200 ml), and sodium hydroxide (4 g=0.1 mole) dissolved in water (10 ml) was added. The material did not completely dissolve. Sodium borohydride was added in portions with stirring under a nitrogen atmosphere. The starting material underwent vivid color changes to orange and then to blue with the addition of each portion of reducing agent. The mass became difficult to stir. Eventually, the reaction mixture became more liquid, though the orange color kept returning after each portion was added, as the rather insoluble starting material underwent the first reduction step. The reaction mixture was kept overnight under an atmosphere of nitrogen. The reduction was continued the next day by heating the mixture to near reflux temperature while sodium borohydride was being added. When the stage was reached where the reaction turned colorless after a portion was added and the orange color did not return upon further stirring (after the addition of 6.65 g=0.175 mole sodium borohydride), the mixture was cooled to ≃10° C. and concentrated hydrochloric acid (50 ml=0.5 mole) was added in one portion. The mixture turned orange, then yellow, and a copious beige precipitate formed. This was stirred for 45 minutes and then collected by filtration to yield 27.5 g solids. On recrystallization from methanol (300 ml), using Celite ® to clarify the solution, there were obtained 13.5 g, 81.9% of theory, cream colored needles, m.p. 130°–145° C. (dec.).

EXAMPLE 17

5-Hydroxy-2-methyl-3H-benzotellurazolium Chloride $R^1=OH, R^2=H, X=Cl$ $C_8H_8ClNOTe$      mw=297.23

1,1,1-Trichloro-6-hydroxy-3-methyl-2,1,4-benzoxatellurazinium, inner salt (Example 11) (19.2 g=0.05 mole) was dissolved in methanol (200 ml) with addition of sodium hydroxide (4 g) in water (20 ml). The reduction was carried out under a nitrogen atmosphere, using sodium borohydride (4.3 g=0.11 mole), after the addition of which the solution became clear. The reaction mixture was cooled to ≃10° C., and concentrated hydrochloric acid (65 ml) was added in one portion. Considerable black precipitate (11.7 g) formed, which was collected by filtration. The filtrate was evaporated to 50 ml and chilled to give a second crop (12.3 g). The products were recrystallized from isopropanol to give a combined yield of 9.45 g, 63.9% of theory, cream colored powder, m.p. 125°–132° C. (dec.).

EXAMPLES 18-25

Examples 18 through 25 illustrate the preparation of benzotellurazoles.

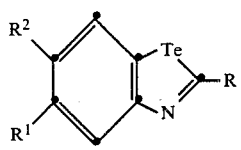

EXAMPLE 18

2-Methylbenzotellurazole $R=CH_3, R^1=R^2=H$ $C_8H_7NTe$      mw=244.74

A mixture of 2-phenylazophenyltellurium trichloride (Preparation A) (20.7 g, 0.05 mole) and ethanol (200 ml) was placed in a 1 liter, 3 necked flask fitted with a nitrogen inlet, a powder addition funnel, and a reflux condenser. To the magnetically stirred mixture was added, under nitrogen, sodium borohydride (7.5 g, 0.2 mole) in increments at a rate sufficient to generate an elevated temperature. When the reaction mixture was nearly colorless the powder funnel was replaced by a stopper, taking care not to interrupt the flow of nitrogen. The flask was then chilled in an ice bath to 5° C. Acetic anhydride (5.5 g, 0.054 mole) was then added, with continued stirring and at such a rate that a temperature of 10° C. was not exceeded in the flask.

The mixture was stirred for another 20 minutes in the ice bath and then 50 ml concentrated aqueous hydrochloric acid was added rapidly. The mixture was stirred for about 10 minutes at room temperature. A black precipitate, which formed during the acid addition, was removed by filtration, washed with ethanol, and discarded, leaving a yellow filtrate.

The yellow filtrate was concentrated under reduced pressure with a bath temperature of about 45° C. When the volume was about 75 ml, the liquid was diluted with water to about 200 ml. The warm solution was clarified by filtration over Celite ® diatomaceous earth and then chilled in ice for two hours. A fluffy, crystalline solid (10.5 g) was collected by filtration. The solid was suspended in water (200 ml), and aqueous ammonium hydroxide was added until precipitation appeared to be complete. The somewhat gummy product was collected by filtration, dried superficially in a stream of air and then recrystallized from about 50 ml of isopropanol using charcoal and Celite ® to give a clear filtered solution. The compound crystallized in rod-like needles, mp 93°–95° C., yield 5.0 g, 41% of theory. Another 0.8 g was obtained from the acidic filtrate by precipitation with ammonia and subsequent diethyl ether extraction.

EXAMPLE 19

5,6-Dimethoxy-2-methylbenzotellurazole $R=CH_3, R^1=R^2=OCH_3$ $C_{10}H_{11}NO_2Te$      mw=304.80

5,6-Dimethoxy-2-methylbenzotellurazolium chloride (Example 12) (10 g) was ground with an equal quantity of sodium bicarbonate and a little water in a mortar until evolution of carbon dioxide ceased. The product was collected by filtration, washed with water and dried in a vacuum to yield ≃8.5 g of colorless powder, m.p. 78°–80° C. Slow crystallization from cyclohexane yielded well defined prisms, m.p. 80°–83° C. The mass spectra and nuclear magnetic resonance spectra were in agreement with that expected for the structural formula.

EXAMPLE 20

5-Methoxy-2-methylbenzotellurazole $R=CH_3, R^1=OCH_3, R^2=H$ $C_9H_9NOTe$      mw=274.77

5-Methoxy-2-methylbenzotellurazolium chloride (Example 13) (3.7 g=0.012 mole) was suspended in water, sodium bicarbonate in excess of that stoichiometrically required was added, and the free base product was extracted with diethyl ether. After washing with saturated sodium sulfate solution, the organic phase was dried and evaporated under reduced pressure to give a residual oil (3.2 g) which was identified by its nuclear magnetic resonance spectra. C, H, N, O and Te elemental analyses were in agreement with that expected for the structural formula.

EXAMPLE 21

2,5-Dimethylbenzotellurazole $R=R^1=CH_3, R^2=H$ $C_9H_9NTe$      mw=258.69

2,5-Dimethylbenzotellurazolium chloride (Example 14) (3.5 g) was treated in an aqueous suspension with sodium bicarbonate in excess of that stoichiometrically required. The free base product was isolated by extraction with diethyl ether and evaporation to dryness. The residue was recrystallized from ≃50 ml isopropanol to yield 1.7 g colorless needles, m.p. 126°–128° C.

EXAMPLE 22

2,5,6-Trimethylbenzotellurazole $R=R^1=R^2=CH_3$ $C_{10}H_{11}NTe$  mw=272.81

2,5,6-Trimethylbenzotellurazolium chloride (Example 15) was converted to the free base product by treatment with sodium carbonate (15 g) in water and extraction with dichloromethane (300 ml). The extract was washed as described above, dried, and evaporated to a cream colored crystalline residue (10.45 g), which was recrystallized from isopropanol (50 ml). A yield of faintly yellow needles, m.p. 101°–103° C. was obtained.

EXAMPLE 23

2-Methyl-5-methylthiobenzotellurazole $R=CH_3, R^1=SCH_3, R^2=H$ $C_9H_9NSTe$  mw=290.84

2-Methyl-5-methylthiobenzotellurazolium chloride (Example 16) (11.5 g=0.035 mole) was suspended in water and sodium bicarbonate in excess of that stoichiometrically required was added. The free base was extracted into dichloromethane. The organic solution was washed with saturated aqueous sodium sulfate, dried, and evaporated in vacuum to a yellow oil (9.06 g). Upon addition of isopropanol (40 ml) the oil crystallized spontaneously to almost white needles to give 8.18 g, 79.8% of theory, m.p. 64°–67° C.

EXAMPLE 24

5-Hydroxy-2-methylbenzotellurazole $R=CH_3, R^1=OH, R^2=H$ $C_8H_7NOTe$  mw=260.75

5-Hydroxy-2-methylbenzotellurazolium chloride (Example 17) (7.45 g) was dissolved in warm water (300 ml) and a slurry of sodium bicarbonate (8 g) in water was added slowly. The free base product separated as a cream colored amorphous solid, which was collected by filtration, washed with water, and dried in a vacuum over Drierite ® brand calcium sulfate drying agent, yield 6.3 g. The material was then recrystallized from isopropanol (50 ml) to give a recovery of ≃4.0 g, m.p. 190°–192° C.

EXAMPLE 25

2-Ethylbenzotellurazole $R=C_2H_5, R^1=R^2=H$ $C_9H_9NTe$  mw=258.76

2-Phenylazophenyltellurium trichloride (Preparation A) (10.4 g, 0.025 mole) was suspended in ethanol (100 ml) in a flask equipped with a nitrogen gas inlet, magnetic stirrer, reflux condenser, and powder addition funnel. While stirring, under a nitrogen atmosphere, at room temperature, sodium borohydride (3.8 g, 0.10 mole) was added in increments at a rate sufficient to maintain a vigorous exothermic reaction. Stirring of the reaction mixture at room temperature was continued for 30 minutes after the addition was complete, maintaining the nitrogen atmosphere. A thermometer was inserted while still maintaining a nitrogen atmosphere and propionic anhydride (3.9 g, 0.03 mole) was added dropwise. The reaction temperature rose from 25° C. to 30° C. Upon completion of the addition, stirring was continued until the temperature returned to 25° C. Concentrated hydrochloric acid (25 ml) was added dropwise to the reaction mixture, resulting in formation of a black solid. The temperature rose to around 50° C. Stirring was continued until the temperature returned to 25° C. The black solid was removed by filtration, and washed with ethanol, and discarded. The filtrate was concentrated in a rotary evaporator, diluted with about an equal volume of water, filtered through a Celite ® pad, and neutralized to a pH of about 7 with sodium bicarbonate. Extraction with diethyl ether and removal of the ether from the extracts left a red, oily semisolid, which was purified by being dissolved in dichloromethane and being applied to a thick layer silica gel chromatography plate. An ultraviolet absorbing substance separated as a pale yellow oil. This was determined to be pure by thin layer chromatography. The infrared and nuclear magnetic resonance spectra were in agreement with that expected for the structural formula.

EXAMPLES 26–28

Examples 26 through 28 illustrate the preparation of naphthotellurazoles.

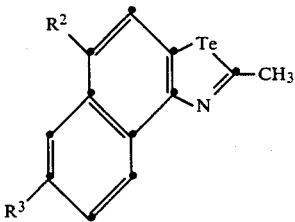

EXAMPLE 26

2-Methylnaphtho[1,2-d]tellurazole $R^3=R^2=H$ $C_{12}H_9NTe$  mw=294.80

3-Chloronaphth[2,1-c][1,2,5]oxatellurazole (Example 2) (48.0 g=0.15 mole) was suspended in a mixture of methanol (150 ml) and tetrahydrofuran (700 ml) in a two liter 3 necked flask fitted with a mechanical stirrer, a condenser, a powder addition funnel, and a nitrogen inlet. The starting compound was reduced by gradual addition of sodium borohydride (14.2 g=0.375 mole) until the reaction mixture was a pale brown. The powder addition funnel was removed and replaced with a stopper. Final addition of sodium borohydride then took place through the condenser until the appearance of the reduced material no longer changed. The mixture was chilled in ice, still under nitrogen, and acetic anhydride (15.3 g=0.15 mole) was added dropwise. The acetylation was permitted to proceed for about 30 minutes. Concentrated hydrochloric acid (75 ml=0.75 mole) was added in one portion. After stirring the mixture, which now contained a black precipitate, for 30 minutes until it reached room temperature, the precipitate was collected by vacuum filtration, rinsed with tetrahydrofuran and air dried.

The solid was then suspended in 350 ml isopropanol, 25 ml concentrated ammonium hydroxide was added, and the mixture was heated to boiling and filtered rapidly with suction. On cooling, needles (18.65 g, 42% of theory) precipitated from the filtrate. For analyses the product was recrystallized once from isopropanol and exhibited m.p. 101°–103° C. Elemental analyses were in agreement with that expected for the structural formula.

EXAMPLE 27

7-Methoxy-2-methylnaphtho[1,2-d]-tellurazole, $R^3 = OCH_3, R^2 = H$ $C_{13}H_{11}NOTe$          mw = 324.83

3-Chloro-7-methoxynaphth[2,1-c][1,2,5]oxatellurazole (Example 5) (17.45 g=0.05 mole) was reduced, acetylated, and treated with hydrochloric acid using the same method and reagent quantities as given for Example 26. Following the procedure described in Example 26, there was obtained 4.93 g, 30.2% of theory, silvery fluffy needles (m.p. 120°–123° C.). The elemental analyses were in agreement with that expected for the structural formula.

EXAMPLE 28

2,5-Dimethylnaphtho[1,2-d]tellurazole $R^3 = H, R^2 = CH_3$ $C_{13}H_{11}NTe$          mw = 308.83

3-Chloro-5-methylnaphth[2,1-c][1,2,5]oxatellurazole (Example 4) (16.7 g=0.05 mole) was suspended in a mixture of tetrahydrofuran (THF, 200 ml) and methanol (40 ml) in a 500 ml three necked flask fitted with a nitrogen inlet, a condenser, and a powder addition funnel. Sodium borohydride was added under a nitrogen atmosphere and in small portions until the reaction mixture was a pale orange yellow. This required about 5 to 6 g. The powder addition funnel was then removed and replaced with a stopper. The reaction mixture was then cooled to 5° C. and acetic anhydride (5.1 g=0.05 mole) added slowly through the condenser. The reaction mixture transiently turned a bright orange. Concentrated hydrochloric acid (25 ml) was then added in one portion, the ice bath removed, and the mixture stirred to room temperature. As the reaction mixture warmed up, a crystalline deposit appeared and was collected by filtration. The crystalline deposit was washed with tetrahydrofuran until the filtrate was colorless and clear. The filtrate was then heated to boiling with a mixture of isopropanol (175 ml) and concentrated ammonium hydroxide (25 ml) and filtered hot with Celite®, the cooled filtrate was diluted with water until crystallization started. A first crop of pale yellow needles (5.06 g), m.p. 110°–112° C. was obtained. A further 1.65 g of product were obtained by two further extractions with the same solvent mixture, giving a total yield of 6.71 g=43.3% of theory. For analysis, the material was recrystallized from isopropanol. This did not change the melting point. Elemental analyses were in agreement with that expected for the structural formula.

EXAMPLE 29

2-Methyl-3H-benzotellurazolium Iodide

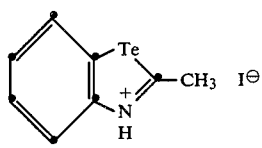

$C_8H_8INTe$          mw = 372.67

To a solution of 2-methylbenzotellurazole (Example 18) (0.81 g, 0.0033 mole) in acetone (25 ml), chilled in an ice bath, was added slowly with stirring 55 mole percent hydriodic acid (1 ml). The product began precipitating from solution. After the addition was complete, the mixture was stirred at ice bath temperature for approximately 10 minutes. The solid was isolated by filtration, washed with diethyl ether, and dried under vacuum at room temperature. Yield 1.13 g (92%) of yellow powder, m.p. 209°–211° C. The C, H, and N elemental analyses and the infrared, nuclear magnetic resonance, and mass spectra of the sample were in agreement with that expected for the structural formula.

EXAMPLES 30–59

Examples 30 through 59 illustrate the preparation of N-alkylated benzotellurazolium salts.

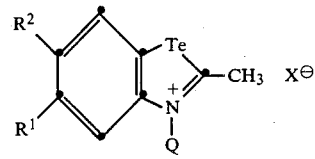

EXAMPLE 30

2,3-Dimethylbenzotellurazolium Trifluoromethanesulfonate $Q = CH_3, R^1 = R^2 = H, X = CF_3SO_3$ $C_{10}H_{10}F_3NO_3STe$          mw = 408.85

2-Methylbenzotellurazole (Example 18) (10.5 g, 0.043 mole) was dissolved in dry dichloromethane (75 ml). Freshly distilled methyl trifluoromethanesulfonate (7.5 g, 0.045 mole) was added to the solution. An exothermic reaction occurred immediately. After a few minutes a crystalline product separated which was collected by filtration, washed with diethyl ether, and dried. Yield 16.86 g (96%). The pale yellow powder was dissolved in acetone (100 ml) and reprecipitated by adding diethyl ether to the solution until it became turbid. Colorless plates separated on chilling. Yield 15.33 g (87% of theory); mp 160°–162° C.

EXAMPLE 31

5,6-Dimethoxy-2,3-dimethylbenzotellurazolium Trifluoromethanesulfonate $Q = CH_3, R^1 = R^2 = OCH_3, X = CF_3SO_3$ $C_{12}H_{14}F_3NO_5STe$          mw = 468.90

5,6-Dimethoxy-2-methylbenzotellurazole (Example 19) (4.8 g=0.013 mole) was dissolved in dichloromethane (75 ml), and methyl trifluoromethanesulfonate (2.48 g=1.66 ml=0.013 mole) was added. The solution turned cloudy and crystals started to deposit within a few minutes. Precipitation was completed by addition of diethyl ether. The product was collected by filtration to give 5.5 g, 86.5% of theory, m.p. 210°–234° C. The product was recrystallized from boiling acetone (≈130 ml required) m.p. 242°–243° C.

The quaternary ammonium salts prepared in Examples 32 through 36 below were all prepared in high yield by combining stoichiometric quantities of the respective base and methyl trifluoromethanesulfonate in dichloromethane, precipitating with diethyl ether, and recrystallization from acetone, with diethyl ether in some instances being added. The C, H, F, N and Te elemental analyses and the nuclear magnetic resonance spectra were consistent with that expected for the structures of each of the quaternary salts.

EXAMPLE 32

5-Methoxy-2,3-dimethylbenzotellurazolium Trifluoromethanesulfonate $Q = CH_3, R^1 = OCH_3, R^2 = H, X = CF_3SO_3$
$C_{11}H_{12}F_3NO_4STe$   mw = 438.87
m.p. 197–198° C.

EXAMPLE 33

2,3,5-Trimethylbenzotellurazolium Trifluoromethanesulfonate $Q = R^1 = CH_3, R^2 = H, X = CF_3SO_3$
$C_{11}H_{12}F_3NO_3STe$   mw = 422.77
m.p. 215–217° C.

EXAMPLE 34

2,3,5,6-Tetramethylbenzotellurazolium Trifluoromethanesulfonate $Q = R^1 = R^2 = CH_3, X = CF_3SO_3$
$C_{12}H_{14}F_3NO_3STe$   mw = 436.91
m.p. 230–233° C.

EXAMPLE 35

2,3-Dimethyl-5-methylthiobenzotellurazolium Trifluoromethanesulfonate $Q = CH_3, R^1 = SCH_3, R^2 = H, X = CF_3SO_3$
$C_{11}H_{12}F_3NO_3S_2Te$   mw = 454.94
m.p. 195–195° C.

EXAMPLE 36

5-Hydroxy-2,3-dimethylbenzotellurazolium Trifluoromethanesulfonate $Q = CH_3, R^1 = OH, R^2 = H, X = CF_3SO_3$
$C_{10}H_{10}F_3NO_4STe$   mw = 424.85
m.p. 171–175° C.

EXAMPLE 37

3-Ethyl-5,6-dimethoxy-2-methylbenzotellurazolium Trifluoromethanesulfonate $Q = C_2H_5, R^1 = R^2 = OCH_3, X = CF_3SO_3$
$C_{13}H_{16}F_3NO_5STe$   mw = 482.93
(15.7 g, 0.005 mole)

5,6-Dimethoxy-2-methylbenzotellurazole (Example 19) was dissolved in chloroform (150 ml). A stoichiometric amount of ethyl trifluoromethanesulfonate was added, and the solution was refluxed for two hours under a condenser protected with a drying tube. After cooling the solution was poured slowly into cold diethyl ether (700 ml) with rapid stirring. The product crystallized and was collected by filtration. Yield 19.3 g (77.3% of theory).

The quaternary salts of the next three examples were obtained in the same general way as that of Example 37, except as noted, using the appropriate benzotellurazole.

EXAMPLE 38

3-Ethyl-5-methoxy-2-methylbenzotellurazolium Trifluoromethanesulfonate $Q = C_2H_5, R^1 = OCH_3, R^2 = H, X = CF_3SO_3$ $C_{12}H_{14}F_3NO_4STe$   mw = 452.90

The alkylation was carried out in diethyl ether at room temperature. Several crops of crystalline product were collected over three days. Total yield 15.0 g (73% of theory).

EXAMPLE 39

3-Ethyl-2,5,6-trimethylbenzotellurazolium Trifluoromethanesulfonate $Q = C_2H_5, R^1 = R^2 = CH_3, X = CF_3SO_3$ $C_{13}H_{16}F_3NO_3STe$   mw = 450.93

The product precipitated directly from chloroform. Yield 16.6 g (91% of theory).

EXAMPLE 40

3-Ethyl-2-methyl-5-methylthiobenzotellurazolium Trifluoromethanesulfonate $Q = C_2H_5, R^1 = SCH_3, R^2 = H, X = CF_3SO_3^{\ominus}$ $C_{12}H_{14}F_3NO_3S_2Te$   mw = 468.96

The product separated from chloroform to which diethyl ether was added to aid precipitation. A gummy residue was recrystallized from ethanol.

EXAMPLES 41–44

Examples 41 through 44 use 2-propen-1-yl trifluoromethanesulfonate in a dry solution of carbon tetrachloride. This was prepared by dissolving trifluoromethanesulfonic anhydride in carbon tetrachloride (about 10 ml of solvent per g of anhydride) and chilling the solution to near 0° C. Under a nitrogen atmosphere a solution of equimolar amounts of 2-propen-1-ol (allyl alcohol) and pyridine in carbon tetrachloride (about 5 ml of solvent per g of anhydride) was added dropwise to the chilled anhydride solution. Stirring was continued for about 30 minutes after the addition was complete, maintaining the nitrogen atmosphere and ice-bath temperature. The reaction mixture was then filtered through a pad of sodium sulfate, and the dried solution was used in the subsequent examples.

EXAMPLE 41

A.

2-Methyl-3-(2-propen-1-yl)benzotellurazolium Trifluoromethanesulfonate $Q = CH_2-CH=CH_2 R^1 = R^2 = H, X = CF_3SO_3$ $C_{12}H_{12}F_3NO_3STe$   mw = 434.90

The dried solution of 2-propen-1-yl trifluoromethanesulfonate (0.008 mole) in carbon tetrachloride was placed in a dropping funnel and added to a solution of 2-methylbenzotellurazole (Example 18) (1.62 g, 0.0066 mole) in dichloromethane (25 ml) under a nitrogen atmosphere at room temperature. After the addition was complete, stirring was continued for 18 hours. The solid was isolated by filtration, washed with diethyl ether, and dried at room temperature under vacuum. Yield 0.43 g (15%), m.p. 90°–93° C. Infrared, nuclear magnetic resonance, and mass spectra were in agreement with that expected for the structural formula.

B.

2-Methyl-3-(2-propen-1-yl)benzotellurazolium Iodide $Q=CH_2-CH=CH_2, R^1=R^2=H, X=I$ $C_{11}H_{12}INTe$  mw=412.73

The solvents from the filtrates above were removed under vacuum and the dark orange semisolid redissolved in acetone (about 30 ml). The solution was stirred, chilled, and treated with a saturated solution of sodium iodide in acetone (about 5 ml). The solid was isolated by filtration, washed with acetone, diethyl ether, and dried. Yield 0.52 g (21% of theory) m.p. 205°–207° C. Elemental analyses and nuclear magnetic resonance spectra were in agreement with that expected for the structural formula.

EXAMPLE 42

5,6-Dimethoxy-2-methyl-3-(2-propen-1-yl)benzotellurazolium Trifluoromethanesulfonate $Q=CH_2-CH=CH_2\ R^1=R^2=OCH_3, X=CF_3SO_3$ $C_{14}H_{16}F_3NO_5STe$  mw=494.95

A dried solution of 2-propen-1-yl tri-fluoromethanesulfonate (0.002 mole) in carbon tetrachloride was added dropwise to a solution of 5,6-dimethoxy-2-methylbenzotellurazole (Example 19) (0.50 g, 0.0016 mole) in dichloromethane (25 ml) under a nitrogen atmosphere at room temperature. After the addition was complete, stirring was continued for 7 hours. The solid was isolated by filtration, washed with diethyl ether, and dried at room temperature under vacuum. Yield 0.38 g. A mass spectrogram of the compound was in agreement with that expected for the structural formula.

EXAMPLE 43

5-Methoxy-2-methyl-3-(2-propen-1-yl)benzotellurazolium Trifluoromethanesulfonate $Q=CH_2CH=CH_2, R^1=OCH_3, R^2=H,$
$X=CF_3SO_3$ $C_{13}H_{14}F_3NO_4STe$  mw=464.92

5-Methoxy-2-methylbenzotellurazole (Example 20) (0.91 g, 0.033 mole), dissolved in dichloromethane (25 ml), was added at room temperature under a nitrogen atmosphere to the solution of 2-propen-1-yl trifluoromethanesulfonate (0.004 mole) from a dropping funnel. The mixture was stirred at room temperature for another 21 hours after the addition was complete, maintaining the nitrogen atmosphere. The solid was isolated by filtration, washed with diethyl ether, and dried at room temperature under vacuum. Yield 0.90 g.

EXAMPLE 44

2,5,6-Trimethyl-3-(2-propen-1-yl)benzotellurazolium Trifluoromethanesulfonate $Q=CH_2CH=CH_2, R^1=R^2=CH_3, X=CF_3SO_3$ $C_{14}H_{16}F_3NO_3STe$  mw=462.94

To a solution of 2,5,6-trimethylbenzotellurazole (Example 22) (9.90 g, 0.0033 mole) in dichloromethane (30 ml) was added the solution of 2-propen-1-yl trifluoromethanesulfonate (0.004 mole) rapidly at room temperature under a nitrogen atmosphere, with good stirring. Solid began separating 10 minutes after the addition was complete. Stirring under a nitrogen atmosphere was continued for about 18 hours. The solid was isolated by filtration, washed with diethyl ether, and dried under vacuum at room temperature. Yield 1.0 g, m.p. 162°–164° C. The mass spectra agreed with the assigned structural formula.

EXAMPLES 45–48

2-Propyn-1-yl trifluoromethanesulfonate was prepared in carbon tetrachloride solution and used as a dried solution in Examples 45 through 48 in the same way that 2-propen-1-yl trifluoromethanesulfonate was prepared and was used in Examples 41 through 44 starting with 2-propyn-1-ol (propargyl alcohol) and trifluoromethanesulfonic anhydride.

EXAMPLE 45

2-Methyl-3-(2-propyn-1-yl)benzotellurazolium Trifluoromethanesulfonate $Q=CH_2C\equiv CH, R^1=R^2=H, X=CF_3SO_3$ $C_{12}H_{10}F_3NO_3STe$  mw=432.87

2-Methylbenzotellurazole (Example 18) (0.81 g, 0.0033 mole) was dissolved in dichloromethane (30 ml). A solution in carbon tetrachloride (25 ml) of 2-propyn-1-yl trifluoromethanesulfonate, prepared as described above, (0.004 mole) was placed in a dropping funnel and added at room temperature under a nitrogen atmosphere to the benzotellurazole solution. The mixture was stirred for about 20 hours after the addition was complete, forming a white solid, which was isolated by filtration, washed with dichloromethane, and dried at room temperature under vacuum. Yield 0.60 g (42% of theory), m.p. 150°–152° C. The infrared, nuclear magnetic resonance and mass spectra were consistent with the structural formula.

EXAMPLE 46

5,6-Dimethoxy-2-methyl-3-(2-propyn-1-yl)benzotellurazolium Trifluoromethanesulfonate $Q=CH_2-C\equiv CH, R^1=R^2=OCH_3, X=CF_3SO_3$ $C_{14}H_{14}F_3NO_5STe$  mw=492.92

5,6-Dimethoxy-2-methylbenzotellurazole (Example 19) (1.0 g, 0.033 mole) was dissolved in dichloromethane (25 ml). The solution of 2-propyn-1-yl trifluoromethanesulfonate, prepared as described above, was added from a dropping funnel under a nitrogen atmosphere. After completion of the addition the mixture was stirred for 16 hours at room temperature. The solid was isolated by filtration, washed with diethyl ether, and dried under vacuum at room temperature. Yield, 1.14 g (70% of theory). The infrared, nuclear magnetic resonance, and mass spectra were in agreement with that expected for the structural formula.

EXAMPLE 47

5-Methoxy-2-methyl-3-(2-propyn-1-yl)benzotellurazolium Trifluoromethanesulfonate $Q=CH_2C\equiv CH$, $R^1=OCH_3$, $R^2=H$, $X=CF_3SO_3$ $C_{13}H_{12}F_3NO_4STe$  mw=462.89

This compound was prepared in the same way and on the same scale as the compound of Example 46, except that 5-methoxy-2-methylbenzotellurazole (Example 20) was used in place of the 5,6-dimethoxy-2-methylbenzotellurazole. Yield 1.23 g, 80% of theory, pale tan powder, m.p. 172°–174° C. (dec). The infrared, nuclear magnetic resonance, and mass spectra were in agreement with that expected for the structural formula.

EXAMPLE 48

2,5,6-Trimethyl-3-(2-propyn-1-yl)benzotellurazolium Trifluoromethanesulfonate $Q=CH_2C\equiv CH$, $R^1=R^2=CH_3$, $X=CF_3SO_3$ $C_{14}H_{14}F_3NO_3STe$  mw=460.93

This compound was prepared in the same way and on the same molar scale as the compound of Example 46, except that 2,5,6-trimethylbenzotellurazole (Example 22) was used in place of 5,6-dimethoxy-2-methylbenzotellurazole. Yield 1.10 g (72% of theory) cream colored powder, m.p. 189°–192° C. dec. The infrared, nuclear magnetic resonance, and mass spectra were in agreement with that expected for the structural formula.

EXAMPLES 49–52

Ethoxycarbonylmethyl trifluoromethanesulfonate was prepared in carbon tetrachloride solution and used as a dried solution in Examples 49 through 52 in the same way that 2-propen-1-yl trifluoromethanesulfonate was prepared and used in Examples 41 through 44, starting with hydroxyacetic acid, ethyl ester (ethyl glycolate).

EXAMPLE 49

3-Ethoxycarbonylmethyl-2-methylbenzotellurazolium Trifluoromethanesulfonate $$Q = CH_2-\overset{O}{\underset{\|}{C}}-OC_2H_5,$$

$R^1=R^2=H$, $X=CF_3SO_3$ $C_{13}H_{14}F_3NO_5STe$  mw=480.91

2-Methylbenzotellurazole (Example 18) (0.81 g, 0.0033 mole) was dissolved in dichloromethane (30 ml). The solution of ethoxycarbonylmethyl trifluoromethanesulfonate (0.004 mole) in carbon tetrachloride prepared as described above, was placed in a dropping funnel and added to the benzotellurazole solution at room temperature under a nitrogen atmosphere. After the addition was complete, the mixture was stirred at room temperature, while maintaining a nitrogen atmosphere for 22 hours. The solid was isolated by filtration and dried at room temperature under vacuum. Yield was 0.62 g (39% of theory) of a white powder, m.p. 156°–158° C. The C, H, N and S elemental analyses and the infrared, nuclear magnetic resonance, and mass spectra were all in agreement with that expected for the structural formula.

EXAMPLE 50

3-Ethoxycarbonylmethyl-5,6-dimethoxy-2-methylbenzotellurazolium Iodide $$Q = CH_2\overset{O}{\underset{\|}{C}}-OC_2H_5,$$

$R^1=R^2=OCH_3$, $X=I$ $C_{14}H_{18}INO_4Te$  mw=518.81

5,6-Dimethoxy-2-methylbenzotellurazole (Example 19) (1.22 g, 0.004 mole) was dissolved in dichloromethane (25 ml). The solution of ethoxycarbonylmethyl trifluoromethanesulfonate (0.004 mole) in carbon tetrachloride, which was prepared as described above, was placed in a dropping funnel and added slowly at room temperature and under a nitrogen atmosphere to the benzotellurazole solution. The reaction mixture was filtered to remove the small amount of solid that had formed. The solvents were removed from the filtrate under reduced pressure, and the residue was redissolved in acetone. The solution was treated with saturated sodium iodide in acetone. This was stirred for 15 minutes. After crystallization began, the mixture was chilled and then filtered. The solid was washed with diethyl ether and dried at room temperature under a vacuum. Yield 0.45 g (22% of theory) of pale yellow crystals, m.p. 184°–186° C. The infrared, nuclear magnetic resonance, and mass spectra were in agreement with that expected for the structural formula.

EXAMPLE 51

Ethoxycarbonylmethyl-5-methoxy-2-methyl-3-benzotellurazolium Iodide $$Q = CH_2\underset{\underset{O}{\|}}{C}OC_2H_5,$$

$R^1=OCH_3$, $R^2=H$, $X=I$ $C_{13}H_{16}INO_3Te$  mw=488.78

This compound was prepared in the same way and on the same scale as the compound of Example 50, except that 5-methoxy-2-methylbenzotellurazole (Example 20) was used in place of 5,6-dimethoxy-2-methylbenzotellurazole. Yield 0.45 g (28% of theory) of a greenish yellow powder, m.p. 215°–217° C. (dec). The infrared, nuclear magnetic resonance, and mass spectra were in agreement with that expected for the structural formula.

EXAMPLE 52

3-Ethoxycarbonylmethyl-2,5,6-trimethylbenzotellurazolium Trifluoromethanesulfonate

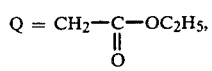

$R^1 = R^2 = CH_3$, $X = CF_3SO_3$ $C_{15}H_{18}F_3NO_5STe$  mw = 508.96

2,5,6-Trimethylbenzotellurazole (Example 22) (0.90 g, 0.0033 mole) was dissolved in dichloromethane (25 ml). A solution of ethoxycarbonylmethyl trifluoromethanesulfonate was placed in a dropping funnel and added rapidly to the benzotellurazole solution, at room temperature and under a nitrogen atmosphere. Stirring was continued for 20 hours after the addition was complete at room temperature while maintaining a nitrogen atmosphere. The solid was isolated by filtration, washed with diethyl ether, and dried at room temperature under vacuum. Yield 0.83 g (49% of theory) of gray-white powder, m.p. 177°–179° C. (dec). The infrared, nuclear magnetic resonance, and mass spectra were in agreement with that expected for the structural formula.

An additional quantity of the compound as the iodide salt was obtained by removing the solvents from the filtrate under reduced pressure, redissolving the residue in acetone, and treating with a saturated solution of sodium iodide in acetone. The yellow solid which formed was isolated by filtration, washed, and dried as before. Yield 0.30 g, m.p. 222°–224° C. (dec.). The various spectra were also in agreement with that expected for the structural formula.

EXAMPLES 53–55

Benzyl trifluoromethanesulfonate was prepared in carbon tetrachloride solution and used as a dried solution in Examples 53 through 55, in the same way the 2-propen-1-yl trifluoromethanesulfonate was prepared and used in Examples 41 through 44, starting with benzyl alcohol and trifluoromethanesulfonic anhydride.

EXAMPLE 53

3-Benzyl-2-methylbenzotellurazolium Trifluoromethanesulfonate

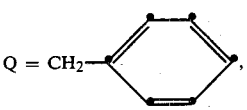

$R^1 = R^2 = H$, $X = CF_3SO_3$ $C_{16}H_{14}F_3NO_3STe$  mw = 484.94

2-Methylbenzotellurazole (Example 18) (0.81 g, 0.0033 mole) was dissolved in dichloromethane (25 ml). The solution of benzyl trifluoromethanesulfonate (0.004 mole) in carbon tetrachloride, prepared as described above, was placed in a dropped funnel and added at room temperature under a nitrogen atmosphere to the benzotellurazole solution. Stirring was continued for 18 hours at room temperature after the addition was complete, maintaining a nitrogen atmosphere. The solid was isolated by filtration, washed with diethyl ether, and dried at room temperature under a vacuum. Yield 0.30 g (19% of theory) of a white powder, m.p. 120°–122° C. The infrared, nuclear magnetic resonance, and mass spectra of this compound were in agreement with that expected for the structural formula.

EXAMPLE 54

3-Benzyl-5,6-dimethoxy-2-methylbenzotellurazolium Trifluoromethanesulfonate

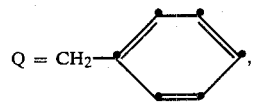

$R^1 = R^2 = OCH_3$, $X = CF_3SO_3$ $C_{18}H_{18}F_3NO_5STe$  mw = 544.99

This compound was prepared in the same way and on the same scale as the compound of Example 53, except that 5,6-dimethoxy-2-methylbenzotellurazole (Example 19) was used in place of 2-methylbenzotellurazole. Yield 0.50 g of a pale gray powder, m.p. 179°–182° C. (dec). The infrared, nuclear magnetic resonance, and mass spectra were in agreement with that expected for a mixture of desired compound and the hydro salt 5,6-dimethoxy-2-methylbenzotellurazole.

EXAMPLE 55

3-Benzyl-2,5,6-trimethylbenzotellurazolium Iodide

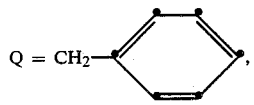

$R^1 = R^2 = CH_3$, $X = I$ $C_{17}H_{18}INTe$  mw = 490.84

This compound was prepared in the same way and on the same scale as the compound of Example 53, except that 2,5,6-trimethylbenzotellurazole (Example 22) was used in place of 2-methylbenzotellurazole and the product which was isolated directly from the reaction mixture was primarily the hydro salt of 2,5,6-tri-methylbenzotellurazole. The solvents were removed from the filtrate under reduced pressure. The residue was redissolved in acetone and treated with a saturated solution of sodium iodide in acetone. The solid isolated was washed and dried as before. Yield 0.10 g, m.p. 203°–206° C. (dec). The infrared and nuclear magnetic resonance spectra were in agreement with that expected for the structural formula.

EXAMPLE 56

2-Methyl-3-[2-(2,2-dimethyl-1,3-dioxolan-4-yl)ethyl]-benzotellurazolium Iodide

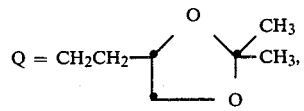

$R^1 = R^2 = H$, $X = I$ $C_{15}H_{20}INO_2Te$  mw=500.84

2-(2,2-Dimethyl-1,3-dioxolan-4-yl)ethyl trifluoromethane sulfonate was prepared in carbon tetrachloride solution and used as a dried solution in this example in the same way as 2-propen-1-yl trifluoromethanesulfonate was prepared and used in Examples 41 through 44, starting with 2,2-di-methyl-4-(2-hydroxyethyl)1,3-dioxolane and trifluoromethanesulfonate.

2-Methylbenzotellurazole (Example 18) (0.81 g, 0.0033 mole) was dissolved in dichloromethane (20 ml), and a solution of 2-(2,2-dimethyl-1,3-dioxolan-4-yl)ethyl trifluoromethanesulfonate in carbon tetrachloride was added from a dropping funnel at room temperature under a nitrogen atmosphere. After the addition was complete, the mixture was stirred for 21 hours at room temperature while maintaining a nitrogen atmosphere. The reaction mixture was filtered, and the solvent was removed from the filtrate under reduced pressure. The residue was dissolved in a small amount of acetone, and the solution was then treated with a saturated solution of sodium iodide in acetone. Diethyl ether was added to precipitate the product, which was isolated by filtration, washed with diethyl ether, and dried at room temperature under vacuum. The yield of pale yellow powder was 0.67 g (41% of theory), m.p. 158°–160° C. C, H and N elemental analyses and the infrared, nuclear magnetic resonance, and mass spectra of this sample were in agreement with that expected for the structural formula.

EXAMPLES 57–59

The following three compounds, Examples 57 through 59, were prepared by the same general procedure. The appropriate 2-methylbenzotellurazole base, 2-methylbenzotellurazole for Example 57, 5,6-dimethoxy-2-methylbenzotellurazole for Example 58, and 5-methoxy-2-methylbenzotellurazole for Example 59, was heated with trimethylene sulfate in equimolar amounts at 75° to 80° C. in a flask equipped with a magnetic stirrer and reflux condenser for 18 hours (3 hours in Example 59). The reactants initially formed a melt, but ultimately the mass became solid. After cooling to room temperature the solid was removed and then crushed and stirred in acetone until a uniform slurry was obtained. The solid was isolated by filtration, washed with more acetone and dried at room temperature under a vacuum. At least one product, Example 59, was observed to decompose on standing in air. Infrared, nuclear magnetic resonance, and mass spectra of each of these three examples were in agreement with that expected for the structural formulae.

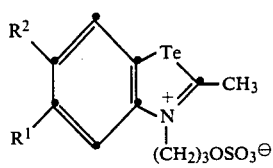

EXAMPLE 57

Anhydro-2-methyl-3-(3-sulfatopropyl)benzotellurazolium Hydroxide $R^1=R^2=H$ $C_{11}H_{13}NO_4STe$  mw=382.88

Yield 79%, tan powder, m.p. 202°–204° C. (dec.).

EXAMPLE 58

Anhydro-5,6-dimethoxy-2-methyl-3-(3-sulfatopropyl)-benzotellurazolium Hydroxide $R^1=R^2=OCH_3$ $C_{13}H_{17}NO_6STe$  mw=442.93

Yield 61%, tan powder, m.p. >250° C.

EXAMPLE 59

Anhydro-5-methoxy-2-methyl-3-(3-sulfatopropyl)benzothiazolium Hydroxide $R^1=OCH_3$, $R^2=H$ $C_{12}H_{15}NO_5STe$  mw=412.91

Yield 79%, tan powder.

EXAMPLES 60–62

Examples 60 through 62 illustrate the preparation of the 3-substituted naphtho[1,2-d]tellurazolium salts:

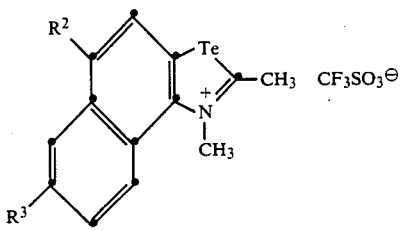

EXAMPLE 60

1,2-Dimethylnaphtho[1,2-d]tellurazolium Trifluoromethanesulfonate $R^3=R^2=H$ $C_{14}H_{12}F_3NO_3STe$  mw=458.92

2-Methylnaphtho[1,2-d]tellurazole (Example 26) (14.8 g=0.05 mole) was dissolved in dry dichloromethane, and methyl trifluoromethanesulfonate (5.52 ml=0.05 mole) was added. The flask was sealed and kept over a weekend. Pale yellow plates (16.1 g, 70% of theory) formed. The product was recrystallized from 150 ml of acetone by addition of diethyl ether (m.p. 178°–183° C.). The mass and nuclear magnetic resonance spectra were in agreement with that expected for the structural formula.

EXAMPLE 61

7-Methoxy-1,2-dimethylnaphtho[1,2-d]tellurazolium Trifluoromethanesulfonate $R^3=OCH_3$, $R^2=H$ $C_{15}H_{14}F_3NO_4STe$  mw=488.93

7-Methoxy-2-methylnaphtho[1,2-d]tellurazole (Example 27) (0.98 g=0.3 mole) was alkylated as described above for Example 60. The reaction mixture was kept at room temperature for 5 days to yield 0.68 g, 46% of

EXAMPLE 62

1,2,5-Trimethylnaphtho[1,2-d]tellurazolium Trifluoromethanesulfonate $R^3=H, R^2=CH_3$ $C_{15}H_{14}F_3NO_3STe$   mw=472.93

2,5-Dimethylnaphtho[1,2-d]tellurazole (Example 28) (0.93 g=0.003mole) was dissolved in dry dichloromethane, and methyl trifluoromethanesulfonate (0.33 ml=0.003 mole) was added. The flask was sealed and kept over a weekend. Bright yellow plates (0.88 g, 61% of theory) formed. The product was recrystallized from 10 ml of acetone by addition of 20 ml of diethyl ether. The melting point was 224°–230° C. The mass and nuclear magnetic resonance spectra were in agreement with that expected for the structural formula.

EXAMPLE 63

1,1,1-Tribromo-3,4-dimethyl-2,1,4-benzoxatellurazinium, inner salt 2,3-Dimethylbenzotellurazolium trifluoromethylsulfonate (2.0 g, 0.005 mole) was dissolved in water and a minimum amount of methanol. Bromine (1.2 g., 010075 mole) in water (1 ml) was added. The yellow precipitate which formed was isolated by filtration. The yield was 1.2 g. The product was recrystallized from acetonitrile using diethyl ether to aid in reprecipitation. The yield was 0.64 g.

EXAMPLE 64

1,1,1-Tribromo-4-ethyl-3,6-di-methyl-2,1,4-benzoxatellurazinium, inner salt $C_{11}H_{14}Br_3NOTe$   mw=543.54

3-Ethyl-2,5-dimethylbenzotellurazolium trifluoromethanesulfonate (2.0 g., 0.0046 mole) was dissolved in methanol (20 ml). Bromine (1.1 g, 0.0069 mole) dissolved in methanol (10 ml) which was then diluted with water (10 ml) was added dropwise at room temperature while vigorously stirring. An orange to yellow solid began to form when the addition was about one third completed. Stirring was continued for ten minutes after the addition was complete. The solid was isolated by filtration, washed with water, and air dried on a suction funnel for several hours. The yield was 1.34 gr (54% of theory). A 1.05 portion was purified by recrystallization from a 3:1 methanol-water solvent mixture (50 ml). HBr in acetic acid (3 ml) was added to the cooled solution to initiate crystallization. The infrared and mass spectra were in agreement with that expected for the structural formula.

EXAMPLE 65

1,1,1-Tribromo-4,6,7-trimethyl-3-methylthio-2,1,4-benzotellurazinium, inner salt $C_{11}H_{14}Br_3NOSTe$   mw=575.60

3,5,6-Trimethyl-2-methylthiobenzotellurazolium trifluoromethanesulfonate (2.0 g, 0.0049 mole) was dissolved in 1:1 methanol-water solvent mixture (75 ml). Bromine (0.79 g, 0.0049 mole), dissolved in methanol (5 ml), was added dropwise at room temperature while stirring vigorously. Stirring was continued for 30 minutes after the addition was complete. The solid which separated was isolated by filtration, washed with methanol and ethyl ether, and air dried. The yield was 1.91 g. (67% of theory). The compound was purified by recrystallization from a 1:1 methanol-water mixture (75 ml). HBr in acetic acid (about 7 ml) was added dropwise to the chilled solution to initiate recrystallization. The infrared and mass spectrum were in agreement with that expected for the structural formula.

EXAMPLE 66

1,1,1-Trichloro-4-ethyl-3,6-dimethyl-2,1,4-benzoxatellurazinium, inner salt $C_{11}H_{14}Cl_3NOTe$   mw=410.11

3-Ethyl-2,5-dimethylbenzotellurazolium trifluoroacetate (1.0 g, 0.4023 mole) was dissolved in methanol (10 ml). Chlorine gas was injected into the solution until chlorine was visible above the solution surface (about 15 minutes). By this time considerable precipitate had formed. The solids were isolated by filtration, washed lightly with methanol then with heptane, and dried at room temperature for three days. The yield of solid was 0.53 g. which represented a 56% yield. The product was purified by redissolving the solid in hot tetrahydrofuran (10 ml), filtering the hot solution, then cooling, and adding heptane to the filtrate until a slight cloudiness appeared. Crystallization was induced, and the solid which had precipitated at the end of about 30 minutes was isolated by filtration and dried. The mass spectrum and the C, HCl and N elemental analyses were in agreement with those expected for the structural formula.

EXAMPLE 67

Evaluation of Antifoggant Activity

Compound 1 was evaluatd in a sulfur plus gold sensitized silver bromoiodide emulsion. The compounds were added at the levels indicated and coated on cellulose acetate support to achieve silver coverage of 4.9 g/m² and gelatin coverage of 11.1 g/m². Samples of the coatings were exposed to a tungsten light source in an Eastman 1B Sensitometer through a wedge spectrograph. The coatings were developed for five minutes in an Elon®(N-methyl-p-aminophenol hemisulfate)-hydroquinone developer, fixed, washed and dried. Samples of each of the coatings were incubated for two weeks at 49° C. and 50% relative humidity before being exposed and processed as above. A density vs log exposure curve was plotted for each coating. The sensitivity and fog (D-min) data were determined from these curves. In addition to compound 1, compound 2, a compound not of this invention, and 4-hydroxy-6-methyltetraazaindene, sodium salt 3, a known antifoggant, were evaluated in the same way using the same emulsion and processing conditions. The results of the evaluations are tabulated in Table I below.

TABLE I

| Com- | Level | Fresh | | After Incubation | |
|---|---|---|---|---|---|
| pound | m/mAg × $10^4$ | Sensitivity | Fog | Sensitivity | Fog |
| Control | None | 100 | 0.12 | 68 | 0.44 |
| 1 | 0.05 | 94 | 0.12 | 82 | 0.34 |
|  | 0.15 | 89 | 0.12 | 112 | 0.24 |
|  | 0.50 | 85 | 0.12 | 123 | 0.14 |
| 2 | 0.05 | 91 | 0.13 | 94 | 0.32 |
|  | 0.15 | 95 | 0.11 | 132 | 0.19 |
|  | 0.50 | 85 | 0.12 | 95 | 0.10 |
| 3 | 0.05 | 87 | 0.12 | 68 | 0.43 |
|  | 0.15 | 95 | 0.12 | 71 | 0.40 |
|  | 0.50 | 74 | 0.11 | 94 | 0.31 |

The results show unequivocally that compound 1 of this invention is very effective as an antifoggant and like compound 2 is effective at significantly lower levels than the well-known antifoggant 3. Also, the antifoggant activity is achieved without loss of sensitivity and indeed, on incubation, compound 1 appears to be enhancing sensitivity at the levels used.

The invention has been described in detail with particular reference to preferred embodiments thereof, but it will be understood that variations and modifications can be effected within the spirit and scope of the invention.

What is claimed is:

1. A photographic element containing a radiation sensitive silver halide emulsion and an effective amount of a fog inhibiting agent characterized in that the fog inhibiting agent is a quaternized aromatic oxatellurazinium salt.

2. A photographic element according to claim 1 further characterized in that said silver halide emulsion contains surface latent image forming silver halide grains.

3. A photographic element according to claim 2 further characterized in that said silver halide grains are surface chemically sensitized.

4. A photographic element according to claim 2 further characterized in that said silver halide grains are spectrally sensitized.

5. A photographic element according to claim 1 further characterized in that said aromatic oxatellurazinium salt is comprised of a quaternized 1,2,5-oxatellurazinium ring fused with a carbocyclic aromatic ring.

6. A photographic element according to claim 5 further characterized in that said oxatellurazinium salt is a quaternized 2,1,4-benzoxatellurazinium salt.

7. A photographic element according to claim 1 further characterized in that said oxatellurazinium salt is incorporated in said silver halide emulsion.

8. A photographic element according to claim 7 further characterized in that said oxatellurazinium salt is present in a concentration of from 0.005 to 5.0 millimole per silver mole.

9. A photographic element according to claim 8 further characterized in that said oxatellurazinium salt is present in a concentration of from 0.01 to 0.5 millimole per silver mole.

10. A photographic element according to claim 1 further characterized in that said quaternized oxatellurazinium salt satisfies the formula

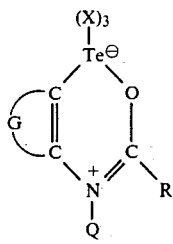

wherein:
G represents the atoms completing an aromatic nucleus,
R represents hydrogen, an aliphatic or aromatic group comprised of a hydrocarbon moiety optionally linked through a divalent oxy, thio, or carbonyl linkage, an amino group, an amido group, a ureido group, a formamidine disulfide group, or a —C(O)M group, wherein M is chosen to complete an aldehyde, acid, ester, thioester, or salt,
Q represents a quaternizing substituent, and
X represents halogen or pseudohalogen.

11. A photographic element according to claim 10 further characterized in that G represents the atoms completing a fused benzo or naphtho nucleus.

12. A photographic element according to claim 11 further characterized in that X is bromide or chloride.

13. A photographic element according to claim 12 further characterized in that R is an alkyl group.

14. A photographic element according to claim 10 further characterized in that said quaternizing substituent is comprised of an optionally substituted hydrocarbon moiety.

15. A photographic element according to claim 14 further characterized in that said hydrocarbon moiety is substituted with an oxy, thio, sulfo, sulfonyl, sulfato, or carboxy group, or a halogen atom.

16. A photographic element according to claim 14 wherein said hydrocarbon moiety is an alkyl moiety.

17. A photographic element according to claim 16 wherein said alkyl moiety contains from 1 to 6 carbon atoms.

18. A photographic element according to claim 10 wherein said quaternizing substitutent is a sulfoalkyl or sulfatoalkyl radical.

19. A photographic element according to claim 10 wherein said quaternizing substituent is comprised of an aralkyl radical.

20. A photographic element according to claim 10 wherein said quaternizing substituent contains an ester linkage.

21. A photographic element according to claim 10 wherein said quaternizing substituent includes a dioxolane ring.

22. A process of producing a photographic image comprising developing a photographic element containing at least one imagewise exposed silver halide emulsion layer in the presence of an effective amount of a fog inhibiting agent characterized in that the fog inhibiting agent is a quaternized aromatic oxatellurazinium salt.

23. A process of producing a photographic image according to claim 22 further characterized in that said quaternized oxatellurazinium salt is introduced into said photographic element prior to or during development of said imagewise exposed silver halide emulsion layer.

24. A process of producing a photographic image according to claim 23 further characterized in that said quaternized oxtellurazinium salt is initially present in a processing solution in a concentration of from 0.05 to 0.5 millimole per liter.

25. A process of producing a photographic image according to claim 22 further characterized in that said quaternized oxatellurazinium salt is initially present in a hydrophilic colloid layer of said photographic element.

26. A process of producing a photographic image according to claim 25 further characterized in that said quaternized oxatellurazinium salt is initially present in a radiation sensitive silver halide emulsion layer.

* * * * *